US011541040B2

(12) United States Patent
Yamaguchi et al.

(10) Patent No.: US 11,541,040 B2
(45) Date of Patent: *Jan. 3, 2023

(54) MEDICINE FOR IMPROVING STATE OF PREGNANCY, AND USE THEREOF

(71) Applicant: Koushi Yamaguchi, Tokyo (JP)

(72) Inventors: Koushi Yamaguchi, Tokyo (JP); Koji Nakagawa, Tokyo (JP)

(73) Assignee: Kouchi Yamaguchi, Tokyo (JP)

( * ) Notice: Subject to any disclaimer, the term of this patent is extended or adjusted under 35 U.S.C. 154(b) by 318 days.

This patent is subject to a terminal disclaimer.

(21) Appl. No.: 16/547,390

(22) Filed: Aug. 21, 2019

(65) Prior Publication Data

US 2019/0374517 A1   Dec. 12, 2019

Related U.S. Application Data

(63) Continuation-in-part of application No. 16/208,336, filed on Dec. 3, 2018, now abandoned, which is a continuation of application No. 15/522,774, filed as application No. PCT/JP2015/080441 on Oct. 28, 2015, now Pat. No. 10,143,682.

(60) Provisional application No. 62/069,472, filed on Oct. 28, 2014.

(51) Int. Cl.
*A61K 31/436* (2006.01)
*A61P 15/08* (2006.01)

(52) U.S. Cl.
CPC ............ *A61K 31/436* (2013.01); *A61P 15/08* (2018.01)

(58) Field of Classification Search
CPC .............................. A61K 31/436; A61P 15/08
USPC ....................................................... 514/291
See application file for complete search history.

(56) References Cited

U.S. PATENT DOCUMENTS

2014/0113928 A1    4/2014  Albaghdadi et al.
2017/0333402 A1*  11/2017  Yamaguchi ........... A61K 31/436

FOREIGN PATENT DOCUMENTS

| JP | 03-504640 A | 10/1991 |
| JP | 07-502755 A | 3/1995 |
| JP | 2013-528052 A | 7/2013 |
| WO | 2012/162796 A1 | 12/2012 |

OTHER PUBLICATIONS

Arias-Diaz et al., "Both tacrolimus and sirolimus decrease Th1/Th2 ratio, and increase regulatory T Tymphocytes in the liver after ischemia/reperfusion", Laboratory Investigation, 2009, vol. 89, pp. 433-445 (14 pages total).

Office Action dated Jun. 9, 2020 in Japanese Application No. 2016-556606.
Saito et al., "Pregnancy phenomenon from the perspective of Th1/Th2 balance", Japan Speaking The Japanese Society for Immunology Magazine, 2002, vol. 17, No. 1, pp. 1-9 (13 pages total).
J.A. Garcia-Donaire et al., "Tacrolimus as Basic Immunosuppression in Pregnancy After Renal Transplantation, A Single-Center Experience", Transplantation Proceedings, vol. 37, pp. 3754-3755, 2005 (3 pages total).
Siu Chui Ng et al., "Expression of Intracellular Th1 and Th2 Cytokines in Women with Recurrent Spontaneous Abortion, Implantation Failures after IVF/ET or Normal Pregnancy", American Journal of Reproductive Immunology, vol. 48, 2002, pp. 77-86 (11 pages total).
Cohen, J. et al., Immunosuppression supports implantation of zona pellucida dissected human embryos, Fertil. Steril. 1990, 53(4), p. 662-5.
Garcia-Donaire, J. A. et al., Tacrolimus as basic immunosuppression in pregnancy after renal transplantation, A Single-center experience, Transplant Proc., 2005, 37(9), p. 3754-5.
Hiroshi Fujiwara et al., "Implantation failure", Obstetrical and Gyneocological Therapy, 1999, 78(4), pp. 399 to 403.
International Search Report of International Patent Application No. PCT/JP2015/080441 completed Jan. 5, 2016 and dated Jan. 19, 2016 (4 pages).
Juri Yano et al., "Improvement of Implantation Rate of IVF-ET by Using Prednisolone", Japanese Journal of Fertility and Sterility, 1996, 41(2), p. 191-5.
Kwak-kim JY et al., Increased T helper 1 cytokine responses by circulating T cells are present in women with recurrent pregnancy losses and in infertile women with multiple implantation failures after IVF, Dec. 9, 2002.
Ng SC et al., Expression of Intracellular Th1 and Th2 Cytokines in Women with Recurrent Spontaneous Abortion Implantation Failures after IVF/ET or Normal Pregnancy, Jul. 4, 2002.
Polak de Fried et al., Human reproduction, 1993, 8(3), 393-395.
Polak De Fried,. E et al, Improvement of clinical pregnancy rate and implantation rate of in-vitro fertilization-embryo transfer patients by using methylprednisone, Hum. Reprod., 1993, 8(3), p. 393-5.
Saito S et al., Th1/Th2/Th17 and Regulatory T-Cell Paradigm in Pregnancy, Mar. 5, 2010.
Shinpei Kasakura., "Seishoku to Cytokine Overview Cytokine Kenkyu to Seishoku Men'eki", Horm. Front. Gynecol. 2003, 10(1), pp. 11 to 28.
Uemura Y et al., "Role of human non-invariant NKT lymphocytes in the maintenance of type 2 T helper environment during pregnancy", Dec. 28, 2007.
Yamaguchi K et al., Relationship of Th1/Th2 Cell Balance With the Immune Response to Influenza Vaccine During Pregnancy, Jul. 9, 2009.
Yasumori Izumi et al: "Safety of Tacrolimus Treatment during Pregnancy and Lactation in Systemic Lupus Erythematosus: A Report of Two Patients", Tohoku Journal of Experimental Medicine., vol. 234, No. 1, Jan. 1, 2014 (Jan. 1, 2014), pp. 51-56, XP055474811, JP ISSN: 0040-8727, DOI: 10.1620/tjem.234.51.
Nakagawa Koji et al: "Immunosuppression with Tacrolimus Improved Reproductive Outcome of Women with Repeated Implantation Failure and Elevated Peripheral Blood Th1/Th2 Cell Ratios",American Journal of Reproductive Immunology, vol. 73, No. 4, Apr. 2015 (Apr. 2015), pp. 353-361.

(Continued)

*Primary Examiner* — Yevgeny Valenrod
(74) *Attorney, Agent, or Firm* — Sughrue Mion, PLLC

(57) ABSTRACT

A medicine for improving the state of pregnancy, which comprises a compound represented by general formula (I) or a pharmaceutically acceptable salt thereof as an active ingredient; and a use of the medicine.

9 Claims, 1 Drawing Sheet

(56) References Cited

OTHER PUBLICATIONS

Tacrolimus Capsules FDA labe 2009 (Year: 2009).
European Search Opinion of related European Patent Application No. 15 854 164.9 dated Jun. 8, 2018.
Supplementary European Search Report of related European Patent Application No. 15 854 164 completed May 30, 2018 and dated Jun. 8, 2018 (3) pages.

* cited by examiner

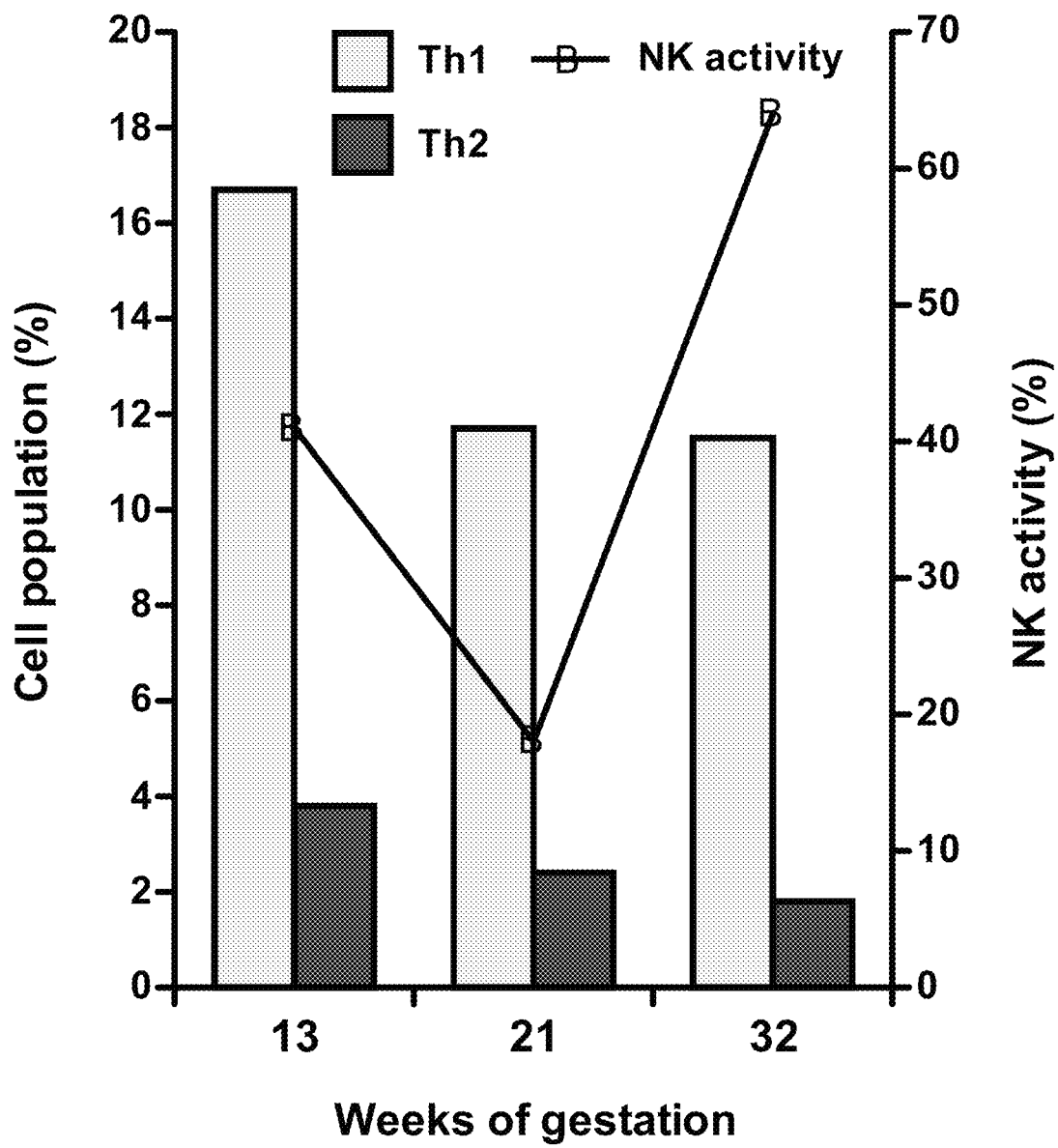

MEDICINE FOR IMPROVING STATE OF PREGNANCY, AND USE THEREOF

CROSS-REFERENCE TO RELATED APPLICATIONS

This is a Continuation-in-Part of U.S. application Ser. No. 16/208,336 filed Dec. 3, 2018, which is a Rule 53(b) Continuation of application Ser. No. 15/522,774 filed Jun. 28, 2017, which is a 371 of International Application No. PCT/JP2015/080441 filed Oct. 28, 2015, claiming priority based on U.S. Provisional Application No. 62/069,472 filed Oct. 28, 2014, the contents of all of which are incorporated herein by reference in their entirety.

TECHNICAL FIELD

The present invention relates to a medicine or a medical agent for ameliorating pregnancy conditions including sterility and/or infertility, the medicine including a particular immunosuppressive component, and utilization of the medicine.

BACKGROUND ART

There are a large number of people who have finally given up bearing children even though they hope for bearing children, because they are incapable of normal pregnancy or childbearing. When the condition of being incapable of normal pregnancy or childbearing is categorized by stages, the condition can be divided into a condition in which implantation of a fertilized ovum into the endometrium does not proceed properly, and pregnancy is not established (sterility in a broad sense); and a condition in which implantation of a fertilized ovum into the endometrium proceeds properly, but a child is not born due to miscarriage, stillbirth, and the like (infertility in a broad sense).

Sterility and infertility may be considered as subjects for treatment as so-called infecundity and infertilitas, when the condition sets in. Under the current circumstances, for the treatment of infecundity and infertilitas, therapeutic methods that are considered optimal are selected according to the causes. For example, in the case of infecundity and infertilitas caused by blood coagulation disorder, diagnostic methods and therapeutic indicators are available, and the therapeutic methods have been almost established. However, for the reason that infecundity and infertilitas without clearly specified causes also exist at a considerable proportion, clinicians often need to struggle to find proper treatments. For example, under severe infecundity, there exist cases with disorder of implantation, in which impregnation fails even though treatment based on in vitro fertilization is attempted several times. Under severe infertilitas, there exist numerous cases in which subjects are resistant to the therapy for infertilitas that is currently implemented. There are no special therapeutic methods in connection with severe infecundity that is considered cryptogenic; however, in connection with severe infertilitas, for example, antiplatelet therapy (administration of low-dose aspirin), anticoagulation therapy (administration of heparin), steroid therapy (PSL; prednisolone), and large-quantity gamma-globulin therapy (IVIG) may be carried out.

CITATION LIST

Non Patent Literature

Non Patent Literature 1: Uemura Y, Suzuki M, Liu T Y, Narita Y, Hirata S, Ohyama H, Ishihara O., Matsushita S. Int Immunol. 2008; 20: 405-12.

Non Patent Literature 2: Saito S, Nakashima A, Shima T, Ito M. Am J Reprod Immunol. 2010; 63: 601-10.

Non Patent Literature 3: Kwak-Kim J Y, Chung-Bang H S, Ng S C, Ntrivalas E I, Mangubat C P, Beaman K D, Beer A E, Gilman-Sachs A. Hum Reprod. 2003; 18: 767-73.

Non Patent Literature 4: Ng S C, Gilman-Sachs A, Thaker P, Beaman K D, Beer A E, Kwak-Kim J. Am J Reprod Immunol. 2002 August; 48 (2): 77-86.

Non Patent Literature 5: Yamaguchi K, Hisano M, Isojima S, Irie S, Arata N, Watanabe N, Kubo T, Kato T, Murashima A. J Med Virol. 2009; 81: 1923-8.

BRIEF DESCRIPTION OF THE DRAWINGS

FIG. 1 is a graph showing alteration of the Th1 and Th2 cell population in CD4 positive cells and the NK cell activity during pregnancy.

SUMMARY OF INVENTION

Technical Problem

A fertilized ovum or a fetus is a foreign material (a kind of exogenous antigen) to the mother's body. Therefore, it is considered that during the period extending from the implantation of a fertilized ovum and maintenance of pregnancy to the childbirth, changes occur in the immune mechanism of the mother's body in order for the mother's body to continue accepting the fertilized ovum or the fetus without elimination from the mother's body. For example, it is considered that in the intrauterine decidua, it is one important factor for continuing pregnancy to promote the suppression of the immune mechanism centered on cell-mediated immunity in order to prevent exclusion of the fertilized ovum or the fetus as a foreign material (Non Patent Literatures 1 to 5). However, the immune mechanism is very complicated, and the details of the changes occurring in the immune mechanism of the mother's body during the period from the implantation of the fertilized ovum to childbirth still need to be clarified in large part.

Under such circumstances, among existing therapeutic methods, immunosuppressive therapy for the treatment of infecundity does not exist.

For the treatment of infertilitas, it is considered that the steroid (PSL) therapy or large-quantity gamma-globulin therapy (IVIG) can act suppressively on the immune mechanism. However, it has been reported that either therapeutic method has various undesirable influences on the mother's body and the fetus. Furthermore, IVIG therapy also has a problem that there is a risk of unknown infection attributed to the use of a blood plasma fractionation (purified from pooled plasma of 1,000 or more persons), and the operating period is short.

However, it has been gradually clarified by preliminary search of the inventors of the present invention that among the patients of infecundity, there are people who are suspected to undergo an enhancement in the cell-mediated immunity compared to the state before pregnancy and have a rejection reaction against the fertilized ovum at the time of implantation; and among the patients of infertilitas, there are people who do not have abnormalities in the immune state before implantation, but are suspected to undergo a noticeable enhancement in the cell-mediated immunity after implantation (after establishment of pregnancy) and thereby have a rejection reaction against the fetus. In both cases, it is speculated that having insufficient suppressive mechanism for immunity that attacks the fertilized ovum or the fetus (immunological tolerance) is an important factor.

Based on these findings, the inventors of the present invention presumed that reception of a fertilized ovum or an embryo having an isoantigen onto the endometrium could result in an immunoresponse that is very similar to organ transplantation, and attempted to verify this presumption from various angles. As a result, the inventors found a medicine that exhibits an effect of sufficiently ameliorating the conditions of sterility or infertility and with which any undesirable influence on the mother's body or the fetus is suppressed, and thus conceived the present invention. The inventors also found that this medicine may also be helpful for the amelioration of pregnancy conditions other than sterility or infertility, and thus the inventors conceived the present invention.

Hemolysis, elevated liver enzymes, and low platelet count (HELLP) syndrome and eclampsia are often complicated by preeclampsia in hypertension disorders of pregnancy (HDP). In the absence of pre-pregnancy diseases such as chronic hypertension and renal dysfunction, the inducing mechanism for HDP is thought to be a disorder in the construction of the placenta, which could be caused by an abnormal level of maternal-fetal immunity. Although the causes of HELLP syndrome and eclampsia are not completely understood, both diseases are known as complications of eclampsia in HDP[35,36]. When essential maternal problems such as chronic hypertension, renal dysfunction, aging, and obesity are eliminated, the remaining cause of HDP is thought to be the result of a disorder in the construction of the placenta, which could be caused by abnormal maternal-fetal immunity[37-44]. Abnormal maternal-fetal immunity can result in an insufficient inhibition of inversion by cell-mediated or humoral immunity via T cells and in an insufficient level of immune tolerance to fetus antigens[45]. The inventors found that a regimen of tacrolimus can be used to deter an expected onset of HELLP syndrome.

Solution to Problem

In order to solve the problems described above, the present invention includes the following embodiments.

A medicine for ameliorating pregnancy conditions, the medicine including a compound represented by the following General Formula (I) or a pharmaceutically acceptable salt thereof as an active ingredient:

[Chemical Formula 1]

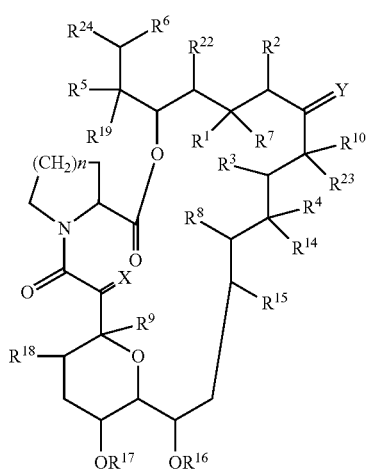

(I)

wherein each of the adjacent pairs of $R^1$ with $R^2$, $R^3$ with $R^4$, and $R^5$ with $R^6$ independently (a) represents two adjacent hydrogen atoms, or $R^2$ may be an alkyl group, or (b) may form another bond between the carbon atoms to which the pair members are respectively bonded;

$R^7$ represents a hydrogen atom, a hydroxyl group, or a protected hydroxyl group, or may be bonded to an alkyl and together represent an oxo group;

$R^8$ and $R^9$ each independently represent a hydrogen atom or a hydroxyl group;

$R^{10}$ represents a hydrogen atom, an alkyl group, an alkyl group substituted with one or more hydroxyl groups, an alkenyl group, an alkenyl group substituted with one or more hydroxyl groups, or an alkyl group substituted with an oxo group;

X represents an oxo group, (a hydrogen atom, a hydroxyl group), (a hydrogen atom, a hydrogen atom), or a group represented by formula: —$CH_2O$—;

Y represents an oxo group, (a hydrogen atom, a hydroxyl group), (a hydrogen atom, a hydrogen atom), or a group represented by formula: N—$NR^{11}R^{12}$ or formula: N—$OR^{13}$;

$R^{11}$ and $R^{12}$ each independently represent a hydrogen atom, an alkyl group, an aryl group, or a tosyl group;

$R^{13}$, $R^{14}$, $R^{15}$, $R^{16}$, $R^{17}$, $R^{18}$, $R^{19}$, $R^{22}$, and $R^{23}$ each independently represent a hydrogen atom or an alkyl group;

$R^{24}$ represents a ring which can include one or more heteroatoms and may be substituted as desired; and n represents 1 or 2, and in addition to the meanings described above, Y, $R^{10}$ and $R^{23}$ may also be bonded together with the carbon atoms to which Y, $R^{10}$ and $R^{23}$ are bonded, and represent a heterocyclic group formed from a saturated or unsaturated 5-membered or 6-membered ring and containing a nitrogen atom, a sulfur atom, and/or an oxygen atom, and the heterocyclic group may be substituted with one or more groups selected from an alkyl group, a hydroxyl group, an alkyloxy group, a benzyl group, a group represented by formula: —$CH_2Se$ ($C_6H_5$), and an alkyl group substituted with one or more hydroxyl groups.

Advantageous Effects of the Invention

According to an embodiment of the present invention, pregnancy conditions including sterility and/or infertility can be ameliorated.

Another embodiment is directed to a treatment of HELLP syndrome of a subject. In an aspect, the subject may be a pregnant mammal, including human.

According to still another embodiment, a method of prolong an onset of HELLP syndrome in a subject. In an aspect, the subject may be a pregnant mammal, including human.

DESCRIPTION OF EMBODIMENTS

Hereinafter, the present invention will be explained in detail.

1. Medicine (Pharmaceutical Composition)

(Active Ingredient)

The medicine according to the present invention includes, as an active ingredient, a compound represented by the following General Formula (I) (hereinafter, these may be collectively referred to as Compound (I)) or a pharmaceutically acceptable salt thereof as an active ingredient.

Compound (I) is a macrolide-based compound. Macrolide-based compound is a generic name for compounds which are large macrocyclic lactones and have 12 or more ring member atoms.

[Chemical Formula 2]

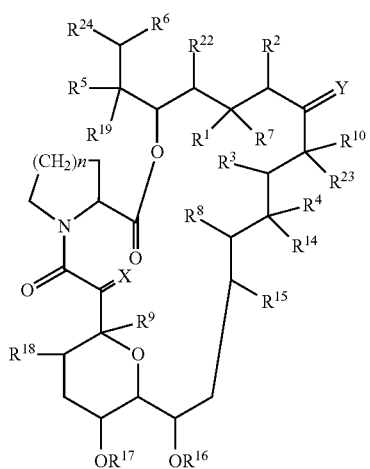

(I)

wherein each of the adjacent pairs of $R^1$ with $R^2$, $R^3$ with $R^4$, and $R^5$ with $R^6$ independently:

(a) represents two adjacent hydrogen atoms, or $R^2$ may be an alkyl group, or (b) may form another bond between the carbon atoms to which the pair members are respectively bonded;

$R^7$ represents a hydrogen atom, a hydroxyl group, or a protected hydroxyl group, or may be bonded to an alkyl and together represent an oxo group;

$R^8$ and $R^9$ each independently represent a hydrogen atom or a hydroxyl group;

$R^{10}$ represents a hydrogen atom, an alkyl group, an alkyl group substituted with one or more hydroxyl groups, an alkenyl group, an alkenyl group substituted with one or more hydroxyl groups, or an alkyl group substituted with an oxo group;

X represents an oxo group, (a hydrogen atom, a hydroxyl group), (a hydrogen atom, a hydrogen atom), or a group represented by formula: —$CH_2O$—;

Y represents an oxo group, (a hydrogen atom, a hydroxyl group), (a hydrogen atom, a hydrogen atom), or a group represented by formula: N—$NR^{11}R^{12}$ or formula: N—$OR^{13}$;

$R^{11}$ and $R^{12}$ each independently represent a hydrogen atom, an alkyl group, an aryl group, or a tosyl group;

$R^{13}$, $R^{14}$, $R^{15}$, $R^{16}$, $R^{17}$, $R^{18}$, $R^{19}$, $R^{22}$, and $R^{23}$ each independently represent a hydrogen atom or an alkyl group;

$R^{24}$ represents a ring which can include one or more heteroatoms and may be substituted as desired; and n represents 1 or 2.

In addition to the meanings described above, Y, $R^{10}$ and $R^{23}$ may also be bonded together with the carbon atoms to which Y, $R^{10}$ and $R^{23}$ are bonded, and represent a heterocyclic group formed from a saturated or unsaturated 5-membered or 6-membered ring and containing a nitrogen atom, a sulfur atom, and/or an oxygen atom, and the heterocyclic group may be substituted with one or more groups selected from an alkyl group, a hydroxyl group, an alkyloxy group, a benzyl group, a group represented by formula: —$CH_2Se$ ($C_6H_5$), and an alkyl group substituted with one or more hydroxyl groups.

Preferable $R^{24}$ may be a cyclo-($C_{5-7}$) alkyl group which may have an appropriate substituent, and examples thereof include, for example, the following groups.

(a) a 3,4-dioxo-cyclohexyl group;

(b) a 3-$R^{20}$-4-$R^{21}$-cyclohexyl group, wherein $R^{20}$ represents a hydroxyl, an alkyloxy, an oxo, or $OCH_2OCH_2CH_2OCH_3$, and $R^{21}$ represents a hydroxyl, —OCN, an alkyloxy, a heteroaryloxy which may have an appropriate substituent, —$OCH_2OCH_2CH_2OCH_3$, a protected hydroxyl, a chloro, a bromo, an iodo, an aminooxalyloxy, an azide group, a p-tolyloxythiocarbonyloxy, or $R^{25}R^{26}$CHCOO-(wherein $R^{25}$ represents a hydroxyl group which may be protected as desired, or a protected amino group; and $R^{26}$ represents a hydrogen atom or a methyl, or $R^{20}$ and $R^{21}$ may be bonded together and form an oxygen atom of an epoxide ring); or (c) a cyclopentyl group, the cyclopentyl group being substituted with a methoxymethyl, a hydroxymethyl protected as desired, an acyloxymethyl (wherein the acyl moiety is a dimethylamino group which may be quaternized as desired, or a carboxyl group which may be esterified as desired), one or more amino and/or hydroxyl groups which may be protected, or an aminooxalyloxymethyl. A preferred example is a 2-formylcyclopentyl group.

The various definitions and specific examples thereof used for General Formula (I), and preferred embodiments thereof will be explained in detail below.

Unless particularly stated otherwise, the term "lower" is intended to mean a group having 1 to 6 carbon atoms.

A preferred example of the alkyl moiety of the "alkyl group" and the "alkyloxy group" may be a linear or branched aliphatic hydrocarbon residue, and examples include lower alkyl groups such as methyl, ethyl, propyl, isopropyl, butyl, isobutyl, pentyl, neopentyl, and hexyl.

A preferred example of the "alkenyl group" may be a linear or branched aliphatic hydrocarbon residue containing one double bond, and examples include lower alkenyl groups such as vinyl, propenyl (allyl or the like), butenyl, methylpropenyl, pentenyl, and hexenyl.

Preferred examples of the "aryl group" include phenyl, tolyl, xylyl, cumenyl, mesityl, and naphthyl.

Preferred protective groups for the "protected hydroxyl group" and the "protected amino" include, for example, 1-(lower alkylthio) (lower) alkyl groups such as a lower alkylthiomethyl groups, such as methylthiomethyl, ethylthiomethyl, propylthiomethyl, isopropylthiomethyl, butylthiomethyl, isobutylthiomethyl, or hexylthiomethyl, with a more preferred example being a $C_1$-$C_4$ alkylthiomethyl group, and the most preferred example being a methylthiomethyl group;

trisubstituted silyl groups, for example, a tri(lower) alkylsilyl such as trimethylsilyl, triethylsilyl, tributylsilyl, tertiary butyl-dimethylsilyl, or tri-tertiary butylsilyl, and for example, a lower alkyldiarylsilyl such as methyldiphenylsilyl, ethyldiphenylsilyl, propyldiphenylsilyl, or tertiary butyldiphenylsilyl, more preferred examples being a tri($C_1$-$C_4$) alkylsilyl group and a $C_1$-$C_4$ alkyldiphenylsilyl group, and the most preferred examples being a tertiary butyl-dimethylsilyl group and a tertiary butyldiphenylsilyl group; and acyl groups such as an aliphatic acyl group derived from a carboxylic acid, a sulfonic acid or a carbamic acid, an aromatic acyl group, and an aliphatic acyl group substituted with an aromatic group.

Examples of the aliphatic acyl group include a lower alkanoyl group which may have one or more appropriate substituents such as a carboxyl, such as formyl, acetyl, propionyl, butyryl, isobutyryl, valeryl, isovaleryl, pivaloyl, hexanoyl, carboxyacetyl, carboxypropionyl, carboxybutyryl, or carboxyhexanoyl;

a cyclo-(lower) alkyloxy-(lower) alkanoyl group which may have one or more appropriate substituents such as a lower alkyl, such as cyclopropyloxyacetyl, cyclobutyloxypropionyl, cycloheptyloxybutyryl, menthyloxyacetyl, menthyloxypropionyl, menthyloxybutyryl, menthyloxypentanoyl, or a menthyloxyhexanoyl;

a camphorsulfonyl group; and a lower alkylcarbamoyl group having one or more appropriate substituents such as a carboxyl or a protected carboxyl, for example, a carboxy-(lower) alkylcarbamoyl group such as carboxymethylcarbamoyl, carboxyethylcarbamoyl, carboxypropylcarbamoyl, carboxybutylcarbamoyl, carboxypentylcarbamoyl or carboxyhexylcarbamoyl, or a tri-(lower) alkylsilyl-(lower) alkyloxycarbonyl-(lower) alkylcarbamoyl group such as trimethylsilylmethoxycarbonyl ethyl carbamoyl, trimethylsilylethoxycarbonylpropylcarbamoyl, triethylsilylethoxycarbonylpropylcarbamoyl, tertiary butyldimethylsilylethoxycarbonylpropylcarbamoyl, or trimethylsilylpropoxycarbonylbutylcarbamoyl group.

Examples of the aromatic acyl group include, an aroyl group which may have one or more appropriate substituents such as a nitro, for example, benzoyl, toluoyl, xyloyl, naphthoyl, nitrobenzoyl, dinitrobenzoyl, or nitronaphthoyl; and an arenesulfonyl group which may have one or more appropriate substituents such as a halogen, for example, benzenesulfonyl, toluenesulfonyl, xylenesulfonyl, naphthalenesulfonyl, fluorobenzenesulfonyl, chlorobenzenesulfonyl, bromobenzenesulfonyl, or iodobenzenesulfonyl.

The aliphatic acyl group substituted with an aromatic group may be, for example, an ar-(lower) alkanoyl group which may have one or more appropriate substituents such as a lower alkyloxy or a trihalo-(lower) alkyl, for example, phenylacetyl, phenylpropionyl, phenylbutyryl, 2-trifluoromethyl-2-methoxy-2-phenylacetyl, 2-ethyl-2-trifluoromethyl-2-phenylacetyl, or 2-trifluoromethyl-2-propoxy-2-phenylacetyl.

Among the acyl groups described above, more preferred acyl groups include a $C_1$-$C_4$ alkanoyl group which may have a carboxyl, a cyclo-($C_5$-$C_6$) alkyloxy-($C_1$-$C_4$) alkanoyl group having two ($C_1$-$C_4$) alkyls in the cycloalkyl moiety, a camphorsulfonyl group, a carboxy-($C_1$-$C_4$) alkylcarbamoyl group, a tri-($C_1$-$C_4$) alkylsilyl-($C_1$-$C_4$) alkyloxycarbonyl-($C_1$-$C_4$) alkylcarbamoyl group, a benzoyl group which may have one or two nitro groups, a benzenesulfonyl group having a halogen, and a phenyl-($C_1$-$C_4$) alkanoyl group having a $C_1$-$C_4$ alkyloxy and a trihalo-($C_1$-$C_4$) alkyl. Among them, the most preferred examples include acetyl, carboxypropionyl, menthyloxyacetyl, camphorsulfonyl, benzoyl, nitrobenzoyl, dinitrobenzoyl, iodobenzenesulfonyl, and 2-trifluoromethyl-2-methoxy-2-phenylacetyl.

Preferred examples of the "heterocyclic group formed from a saturated or unsaturated 5-membered or 6-membered ring and containing a nitrogen atom, a sulfur atom, and/or an oxygen atom" include a pyrrolyl group and a tetrahydrofuryl group.

Regarding the "heteroaryl moiety which may have an appropriate substituent" in the "heteroaryloxy which may have an appropriate substituent", the moieties listed as examples of group R1 of the compound represented by the formula in EP-A-532,088 may be mentioned; however, for example, a 1-hydroxyethylindol-5-yl is preferred. The disclosure of the patent literature is partially incorporated herein by reference.

It is described in, for example, EP-A-184162, EP-A-323042, EP-A-423714, EP-A-427680, EP-A-465426, EP-A-480623, EP-A-532088, EP-A-532089, EP-A-569337, EP-A-626385, WO 89/05303, WO 93/05058, WO 96/31514, WO 91/13889, WO 91/19495, and WO 93/5059 that the compound (I) and a pharmaceutically acceptable salt thereof used for the present invention have excellent immunosuppressive action, antibacterial activity, and other pharmacological activity, and therefore, the compounds are useful for the treatment and prevention of a rejection reaction against the transplantation of an organ or a tissue, a graft-versus-host reaction, an autoimmune disease, an infectious disease, and the like. Furthermore, production methods for those compounds are also disclosed therein. The disclosures are partially incorporated herein by reference.

Particularly, compounds called FR900506 (=FK506, tacrolimus), FR900520 (ascomycin), FR900523 and FR900525 are substances produced by the genus *Streptomyces*, for example, *Streptomyces tsukubaensis* No. 9993 (depository: National Institute of Bioscience and Human-Technology Agency of Industrial Science and Technology, the Ministry of International Trade and Industry, 1-3, Higashi 1-chome, Tsukuba-shi, Ibaraki-ken, Japan (formerly: Fermentation Research Institute, Agency of Industry Science and Technology, the Ministry of International Trade and Industry), date of deposit: Oct. 5, 1984, deposit number: FERM BP-927) or *Streptomyces hygroscopicus* subsp. *yakushmaensis* No. 7238 (depository: National Institute of Bioscience and Human-Technology Agency of Industrial Science and Technology, the Ministry of International Trade and Industry, 1-3, Higashi 1-chome, Tsukuba-shi, Ibaraki-ken, Japan, date of deposit: Jan. 12, 1985, deposit number: FERM BP-928) (EP-A-0184162). Particularly, FK506 (general name: tacrolimus) represented by the following structural formula is a representative compound.

[Chemical Formula 3]

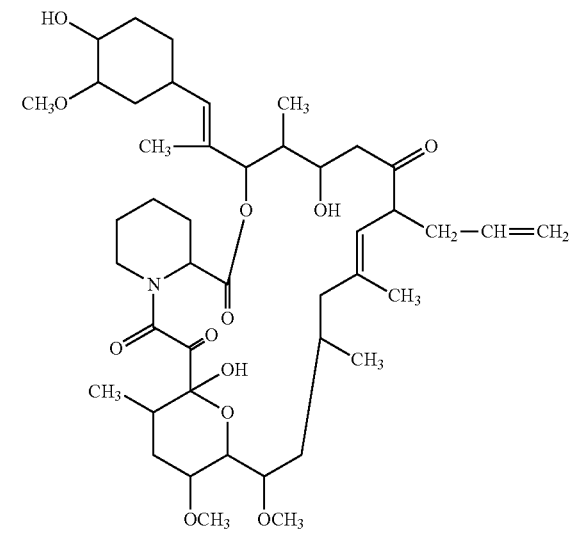

Chemical Name:
17-Allyl-1,14-dihydroxy-12-[2-(4-hydroxy-3-methoxycyclohexyl)-1-methylvinyl]-23,2 5-dimethoxy-13,19,21,27-tetramethyl-11,28-dioxa-4-azatricyclo[22.3.1.04,9]octacos-18-ene-2,3,10,16-tetraone.

Among the examples of Compound (I), more preferred is a compound in which each of the adjacent pairs of $R^3$ with $R^4$ and $R^5$ with $R^6$ forms another bond between the carbon atoms to which the pair members are respectively bonded;

$R^8$ and $R^{23}$ each independently represent a hydrogen atom;

$R^9$ represents a hydroxyl group; $R^{10}$ represents a methyl, ethyl, propyl, or allyl group;

X represents (a hydrogen atom, a hydrogen atom) or an oxo group;

Y represents an oxo group;

$R^{14}$, $R^{15}$, $R^{16}$, $R^{17}$, $R^{18}$, $R^{19}$, and $R^{22}$ each represent a methyl group;

$R^{24}$ represents a 3-$R^{20}$-4-$R^{21}$-cyclohexyl group (wherein $R^{20}$ represents a hydroxyl, an alkyloxy, an oxo, or —$OCH_2OCH_2CH_2OCH_3$; and $R^{21}$ represents a hydroxyl, —OCN, an alkyloxy, a heteroaryloxy which may have an appropriate substituent, a 1-tetrazolyl or a 2-tetrazolyl, —$OCH_2OCH_2CH_2OCH_3$, a protected hydroxyl, a chloro, a bromo, an iodo, an aminooxalyloxy, an azide group, a p-tolyloxythiocarbonyloxy, or $R^{25}R^{26}$CHCOO-(wherein $R^{25}$ represents a hydroxyl group which may be protected as desired, or a protected amino group; and $R^{26}$ represents a hydrogen atom or a methyl), or $R^{20}$ and $R^{21}$ may be bonded together and form an oxygen atom of an epoxide ring; and n represents 1 or 2.

Preferred examples of Compound (I) include tacrolimus, and ascomycin or a derivative thereof, for example, 33-epi-chloro-33-desoxyascomyin described in Example 66a of EP 427,680. Other preferred examples of Compound (I) include, for example, the compound described in Example 6d of EP 569,337 and the compound described in Example 8 of EP 626,385.

The compounds described in EP 0184162, EP 323042, EP 424714, EP 427680, EP 465426, EP 474126, EP 480623, EP 484936, EP 532088, EP 532089, EP 569337, EP 626385, WO 89/05303, WO 93/05058, WO 96/31514, WO 91/13889, WO 91/19495, WO 93/5059, WO 96/31514 and the like may also be mentioned as preferred examples of the macrolide-based Compound (I), and the disclosures of the documents are partially incorporated herein by reference.

According to another embodiment of the present invention, the medicine according to the present invention includes, as an active ingredient, the compound shown below or a pharmaceutically acceptable salt thereof.

Regarding the compound that acts as an active ingredient for the medicine of the present invention, cyclosporins, for example, cyclosporin A, B, D and the like, which are used instead of Compound (I) or a salt thereof, or used in combination with Compound (I) or a salt thereof. These are described in Merck Index (12$^{th}$ edition), No. 2821, the disclosure of which is partially incorporated herein by reference.

A preferred macrolide-based compound that is used as an active ingredient instead of Compound (I) or a salt thereof, or used as an active ingredient in combination with Compound (I) or a salt thereof, for the medicine of the present invention may be rapamycin described in Merck Index (12$^{th}$ edition), No. 8288, or a derivative thereof. Preferred examples thereof include O-substituted derivatives in which the hydroxyl at the 40-position of Formula A in page 1 of WO 95/16691 is substituted by —OR$^1$ (wherein R$^1$ represents a hydroxyalkyl, a hydroalkyloxyalkyl, an acylaminoalkyl, or an aminoalkyl), for example, 40-O-(2-hydroxy) ethyl-rapamycin, 40-O-(3-hydroxy)propyl-rapamycin, 40-O-[2-(2-hydroxy)ethoxy]ethyl-rapamycin, and 40-O-(2-acetaminoethyl)-rapamycin.

These O-substituted derivatives can be produced by a reaction between rapamycin (or dihydro- or deoxorapamycin) and an organic radical bonded to a leaving group (for example, RX (wherein R represents an organic radical that is desirable as an O-substituent such as an alkyl, allyl or benzyl moiety; and X represents a leaving group such as $CC_{13}C(NH)O$ or $CF_3SO_3$).

Regarding the conditions, when X represents $CC_{13}C(NH)O$, the conditions may be acidic or neutral conditions, for example, in the presence of trifluoromethanesulfonic acid, camphorsulfonic acid, p-toluenesulfonic acid, or a pyridinium or substituted pyridinium salt corresponding to such an acid; or when X represents $CF3SO_3$, the conditions may be in the presence of a base such as pyridine, a substituted pyridine, diisopropylethylamine, or pentamethylpiperidine. The most preferred rapamycin derivative is 40-O-(2-hydroxy)ethyl-rapamycin as described in WO 94/09010, the disclosure of which is partially incorporated herein by reference.

Compound (I), rapamycin, and derivatives thereof have similar basic skeletons, namely, tricyclomacrolide skeletons, and at least one similar biological characteristic (for example, immunosuppressive action).

The pharmaceutically acceptable salts of Compound (I), cyclosporin, rapamycin, and derivatives thereof are pharmaceutically acceptable non-toxic salts that are conventionally used, and examples thereof include salts with inorganic or organic bases, such as alkali metal salts such as sodium salts and potassium salts; for example, alkaline earth metal salts such as calcium salts and magnesium salts; ammonium salts; and for example, amine salts such as triethylamine salts and N-benzyl-N-methylamine salts.

Compound (I) of the present invention may have conformers, or one or more pairs of stereoisomers such as optical isomers and geometric isomers attributed to asymmetric carbon atoms and double bonds. Those conformers and isomers are also included in the scope of the compound of the present invention.

Furthermore, Compound (I) may also form a solvate, and in that case, the solvate is also included in the scope of the present invention. Preferred solvates include hydrate and ethanolate.

Other Optional Components

The medicine according to an embodiment of the present invention may also include, in addition to the active ingredient described above, one or more therapeutically active substances having therapeutic action on other diseases, illnesses and conditions, as long as the therapeutically active substances have no risk of inhibiting the activity of the active ingredient and are not harmful to the subject for administration (hereinafter, also referred to as patient).

Furthermore, the medicine of an embodiment of the present invention may also include a pharmaceutically acceptable carrier that is not harmful to the subject for administration. The carrier that can be used may be any of a solid carrier, a semisolid carrier, and a liquid carrier, and may be, for example, any one selected from water, a liquid electrolyte, and a glucose solution, without any particular limitations. The therapeutic medicine may also include auxiliary agents. Examples of the auxiliary agents include a lubricating agent, a stabilizer, an antiseptic agent, an emulsifier, a thickener (viscous agent), a colorant, a fragrance (flavoring agent), an excipient, a preservative, a buffering agent, a corrigent, a suspending agent, an emulsifier, a dissolution aid, and a flow conditioner.

Dosage Form

Examples of the dosage form include a tablet, a capsule, a pill, a granular preparation, a powder, a syrup, a suppository, a troche, a pellet, an emulsion, a suspension, and other known forms. Among these, for example, the dosage form as a preparation for oral administration is preferably any of a tablet, a capsule, a pill, a granular preparation, a powder, a liquid, a syrup, and a jelly; more preferably any of a tablet, a capsule, and a granular preparation; and even more preferably a tablet. As will be described below, the medicine may be formulated as a preparation for parenteral administration such as, for example, an injectable preparation, a suppository, and a percutaneous absorption type preparation.

Method for Producing Medicine

The medicine according to the present invention can be produced by utilizing any known production method. For example, the medicine is produced by preparing an active ingredient and other optional components separately for each component, and then mixing the respective components so as to obtain desired contents.

Subject for Administration for Medicine

Subject Biological Species

The subject for administration of the medicine of the present invention may include a mammal, a bird, a reptile, an amphibian, and the like, and among them, a mammal is preferred. Examples of the mammal include a human being and animals other than human being, including livestock such as cattle, horse, pig, and sheep, and pets such as dog, cat, rat, and rabbit. A preferred subject for administration is a human being. Examples of the bird include poultry such as chicken, wild duck, and domestic duck.

Defective Pregnancy Conditions

The subject for administration of the medicine of the present invention is the above-described subject with defective pregnancy conditions. Here, the term "defective pregnancy conditions" is a concept categorized as an illness or a disease; however, in addition to that, the term is a concept that also includes a state that is defective compared to normal pregnancy. That is, defective pregnancy conditions include the defectiveness of conception in the mother's body and the fetal state, as well as the defectiveness in the health state of the mother's body itself during pregnancy. The term "during pregnancy" refers to an arbitrary period during the term from establishment of pregnancy (synonym for achievement of pregnancy) to childbirth, and includes the whole period of the first trimester of pregnancy, the second trimester of pregnancy, and the third trimester of pregnancy. Here, the first trimester of pregnancy refers to the period from the establishment of pregnancy to the thirteenth week; the second trimester of pregnancy refers to the period from the $14^{th}$ week to the $27^{th}$ week; and the third trimester of pregnancy refers to the period from the $28^{th}$ week to the day of delivery. Furthermore, defective pregnancy conditions include defectiveness in the health state of the mother's body after childbirth, and the health state of the mother's body during pregnancy and after delivery, which appears as disorders in the offspring after birth.

The type of defective pregnancy conditions is not particularly limited; however, specific examples include at least one selected from (1) sterility, (2) infertility, and (3) defective pregnancy conditions other than sterility and infertility (for example, pregnancy complications). Among these, as will be described below, a defective pregnancy condition attributed to immunological abnormalities of the subject for administration is more suitable as the defectiveness to be considered as an object of amelioration by administration of the medicine of the present invention.

Sterility and Infertility

The term "sterility" according to the present specification is used as a meaning in a broad sense, and refers to a state in which the mother's body has difficulties in becoming pregnant compared to the normal state. Sterility is a concept including infecundity. Here, infecundity refers to the case in which pregnancy is not established within one year without contraception under an expectation of childbearing.

According to an embodiment, the subject with sterility, who becomes the subject for administration of the medicine of the present invention, may be receiving an existing treatment for infecundity. Examples of the method for treating such infecundity include artificial insemination, in vitro fertilization, and administration of a fertility medicine.

Among these, specific methods for in vitro fertilization include methods such as embryo transplantation, by which collected ova and sperms are fertilized in a Petri dish, and fertilized ova are transferred back into the womb (In Vitro Fertilization Embryo Transfer: IVF-ET), and Intracytoplasmic Sperm Injection (ICSI), by which fertilization is performed by directly injecting a sperm into an ovum under a microscope. Further examples of IVF-ET include fresh embryo transplantation (fresh ET) of using a fresh embryo for transplantation, and freeze-thawed embryo transplantation (FET) of freezing and thawing an embryo that has been preserved in a frozen state after collection and then using the embryo for transplantation. The subject may be any person who is unable to have pregnancy established (a clear increase in the hCG level is not observed) even if embryo transplantation or intracytoplasmic sperm injection is carried out several times, and the techniques can also be suitably applied to a person who is unable to have pregnancy established even if treatment is carried out three or more times, four or more times, or five or more times.

Causes for sterility including infecundity include an ovum factor, an oviduct factor, a uterine factor, a cervical duct factor, and an immunological factor. Specific examples of the ovum factor include ovulation disorders caused by antiprolactinemia, polycystic ovary syndrome, various stresses, dieting, and premature ovarian dysfunction. Specific examples of the oviduct factor include blockage, stenosis or adhesion of the Fallopian tubes caused by Chladimyal salpingitis and perisalpingitis, and the like. Specific examples of the uterine factor include uterine myoma, endometrial polyp, congenital anomaly of uterus, and intrauterine adhesion (Asherman's syndrome). Specific examples of the cervical duct factor include cervicitis, and abnormal mucus secretion or impaired mucus secretion from the cervical duct. Specific examples of the immunological factor include production of anti-sperm antibodies. Here, sterility of unknown cause implies that all of the above-mentioned factors do not apply, and the cause is not specified. It is considered that sterility of unknown cause includes sterility attributed to immunological abnormalities (including abnormalities in immune cells, and autoimmune diseases such as anti-phospholipid antibody syndrome), and a subject with such sterility of unknown cause is also suitable as a subject for administration of the medicine of the present invention (also see Examples). Particularly, in the case of having an autoimmune disease or in the case of not having an autoimmune disease, a subject with sterility that is presumed to be primarily caused by inhibition of implantation of a fertilized ovum or an embryo into the endometrium due to immunological abnormalities, is suitable as a subject for administration of the medicine of the present invention.

The term "infertility" according to the present specification refers to a state in which after conception, the fetus in the womb of the mother's body is incapable of growing, or a state in which retarded growth or defective growth of the fetus is observed, and the term is a concept including infertilitas. Here, infertilitas refers to the case in which pregnancy (also including spontaneous pregnancy as well as the cases of artificial fertilization and in vitro fertilization) is established, but miscarriage or stillbirth is repeated two or more times so that childbearing is not achieved. Meanwhile, experiencing miscarriage, premature delivery, or stillbirth once, or repeating miscarriage, premature delivery, or stillbirth two times is also included in the concept of "infertility" according to the present invention.

Causes for infertility including infertilitas include a genetic factor, an anatomic factor, an endocrine factor, a coagulative factor, and an autoimmunologic factor. Specific examples of the genetic factor include chromosome aberration of parents, and fetal chromosome aberration. Specific examples of the anatomic factor include myoma and uterine malformation. Specific examples of the endocrine factor include corpus luteum insufficiency, hyperprolactinemia, thyroid dysfunction, and blood sugar abnormalities. Specific examples of the coagulative factor include blood coagulation abnormalities. Specific examples of the autoimmunologic factor include production of anti-phospholipid antibodies (anti-phospholipid antibody syndrome). Here, infertility of unknown cause implies that all of the above-mentioned factors do not apply, and the cause is not specified. It is considered that infertility of unknown cause includes infertility attributed to immunological abnormalities (including abnormalities in immune cells, and autoimmune diseases such as anti-phospholipid antibody syndrome), and a subject with such infertility of unknown cause, or a subject with infertility attributed to an autoimmunologic factor (anti-phospholipid antibody syndrome) is also suitable as a subject for administration of the medicine of the present invention (also see Examples). Particularly, (1) a subject with infertility that is presumed to be primarily caused by enhanced immunological mechanism of excluding a fertilized ovum or an embryo from the mother's body as a foreign material due to immunological abnormalities, and/or (2) a subject with infertility that is presumed to be primarily caused by defective placenta construction due to immunological abnormalities, is suitable as a subject for administration of the medicine of the present invention.

As described above, sterility and infertility accompanied by autoimmune diseases other than anti-phospholipid antibody syndrome are also subject for administration of the medicine of the present invention. Examples of such autoimmune diseases include systemic lupus erythematosus, ANCA-associated vasculitis (cryoglobulinemic vasculitis, IgA vasculitis, hypocomplementemic urticarial vasculitis, polyarteritis nodosa, Kawasaki disease, anti-GBM disease, Takayasu's arteritis, giant cell arteritis, microscopic polyangiitis, granulomatosis with polyangiitis, and eosinophilic granulomatosis with polyangiitis), and malignant rheumatoid arthritis. Autoimmune diseases including anti-phospholipid antibody syndrome may cause defective construction of the placenta through thrombus formation or the like. Defective construction of the placenta may also be accompanied by vasculitis of the placenta and inflammation of the placenta, in addition to thrombus formation. It can be expected to suppress undesirable activity of autoantibodies and to ameliorate defective construction of the placenta, by administering the medicine of the present invention.

Defective Pregnancy Conditions other than Sterility and Infertility

The term "defective pregnancy conditions other than sterility and infertility" according to the present specification includes illnesses or diseases occurring along with pregnancy (pregnancy complications and the like) such as, for example, pregnancy-induced hypertension syndrome, thrombosis, infarction, cardiac failure (peripartum cardiomyopathy or the like), and pulmonary edema; however, the term is a concept that also includes conditions which are defective compared to the normal state of pregnancy, in addition to conditions which are classified as illnesses or diseases. Among these, a subject with a high potential of the onset of pregnancy-induced hypertension syndrome (for example, having an onset history of pregnancy-induced hypertension syndrome) is more suitable as the subject for administration of the medicine of the present invention. Although the mechanism is not clearly known, since the immunological relations between the mother and the child is improved by this treatment, placenta construction proceeds smoothly. Also, since the mother's body is also subjected to less stress, a possibility of avoiding pregnancy complications can also be expected.

Pregnancy-induced hypertension syndrome refers to a syndrome which develops hypertension, which is observed during pregnancy, mainly in the latter half of pregnancy and until the $12^{th}$ week after delivery, or develops hypertension and symptoms such as edema and albuminuria occurring concomitantly with hypertension. The disease type of pregnancy-induced hypertension syndrome is more specifically classified into pregnancy-induced hypertension, preeclampsia, superimposed preeclampsia, and eclampsia. Pregnancy-induced hypertension syndrome is recurrent, and in the case of having a medical history of pregnancy-induced hypertension syndrome during the previous pregnancy, there is a high risk of developing pregnancy-induced hypertension syndrome again during the subsequent pregnancy.

The causes of pregnancy-induced hypertension syndrome include vascular endothelial disorders caused by placental ischemia and a hypoxic state. Therefore, in the case of having pregnancy-induced hypertension syndrome, defective construction of the placenta may occur. Furthermore, as a result, there is a possibility that fetal growth restriction, abruption of the placenta, fetus malfunction, and fetal death may occur.

In the case of a patient of pregnancy-induced hypertension syndrome, it can be expected that rejection against trophoblast, which is a fetal component, is suppressed (suppression of a kind of immunological abnormalities) by administering the medicine of an embodiment of the present invention to the patient, and reconstruction of endometrial spiral arteries into larger spiral arteries is promoted. Therefore, satisfactory construction of the placenta can be promoted.

Age of Subject for Administration of Medicine

The age of the subject for administration may be any age capable of childbearing. When the subject for administration is a human being, for example, the age is preferably from age 16 to age 50, more preferably from age 16 to age 45, and even more preferably from age 16 to age 40. If the age is 16 or higher, consent of the person herself may be obtained. Furthermore, in the case of a sterile patient, since the possibility of secure establishment of pregnancy is higher if the age of the patient is 40 or lower, the effects of the medicine according to the present invention can be obtained more efficiently. The age of the subject for administration is not limited to this; however, for example, the age is from age 30 to age 45, from age 33 to age 43, from age 33 to age 41, or from age 33 to age 39.

More Preferred Examples of Subject for Administration of Medicine

It is preferable that the subject for administration of the medicine described above does not have any disease, illness or condition other than the above-mentioned defective pregnancy conditions, and particularly, it is more preferable that the subject for administration does not have any disease, illness or abnormality related to the uterus, such as submucosal myoma of the uterus, endometrial polyps, intrauterine adhesion, congenital abnormalities in the uterus, and hydrosalpinx. Furthermore, it is preferable that the subject for administration does not have any disease, illness or condition with a high risk of being seriously affected by the medicine of the present invention.

Subject for Administration of Medicine and Th1/Th2 Cell Ratio

According to an embodiment, the Th1/Th2 cell ratio in the subject for administration of the medicine may be determined, and this ratio may be used for the determination of the necessity of the administration of the medicine to a relevant subject or the determination of the dose of the medicine (see Examples for the details of this process). For example, the Th1/Th2 cell ratio in a subject for administration of the medicine is at an increased level compared to a normal person. In a more specific example, a subject whose Th1/Th2 cell ratio has increased by 10% to 800% compared to a normal person is a preferred subject for administration of the medicine of the present invention; a subject whose Th1/Th2 cell ratio has increased by 10% to 400% is a more preferred subject for administration of the medicine of the present invention; and a subject whose Th1/Th2 cell ratio has increased by 10% to 200% may be an even more preferred subject for administration of the medicine of the present invention. Regarding specific values of the Th1/Th2 cell ratio, a subject having a Th1/Th2 cell ratio of 10 to 50 is a preferred subject for administration of the medicine of the present invention, a subject having a Th1/Th2 cell ratio of 10 to 40 is a more preferred subject for administration of the medicine of the present invention, and a subject having a Th1/Th2 cell ratio of 10 to 30 may be an even more preferred subject for administration of the medicine of the present invention. In regard to the Examples that will be described below, the average value of the Th1/Th2 cell ratio of normal persons was about 7 to 8, and the maximum value of the Th1/Th2 cell ratio in a treated group was about 30 to 40.

Here, a normal person refers to an individual who does not have defective pregnancy conditions that serves as a target of amelioration. For example, in a case in which amelioration of sterility is intended, a normal person refers to an individual who does not suffer at least from sterility, and in a case in which amelioration of infertility is intended, a normal person refers to an individual who does not suffer at least from infertility. Preferably, a normal person refers to an individual who does not have defective pregnancy conditions that serve as a target of amelioration, and has not developed any other existing illness or disease (however, may have defective pregnancy conditions other than those conditions serving as targets of amelioration). More preferably, a normal person refers to an individual who does not have all the above-mentioned defective pregnancy conditions, and even more preferably, a normal person refers to an individual who does not have all the above-mentioned defective pregnancy conditions and has not developed any other existing illness or disease.

Without being particularly limited, it is preferable that determination of the Th1/Th2 cell ratio is carried out at a time point between any time immediately before the scheduled day of performing administration of the medicine (the scheduled day, the day before, or two before) and any time after 6 months; a time point between any time immediately before the scheduled day of performing administration of the medicine and any time after 3 months is more preferred; a time point between any time immediately before the scheduled day of performing administration of the medicine and any time after 2 months is even more preferred; and a time point between any time immediately before the scheduled day of performing administration of the medicine and any time after 1 month is particularly preferred. In a more specific example, in a case in which the subject for administration of the medicine is receiving a treatment such as IVF-ET or ICSI, it is preferable to perform determination of the Th1/Th2 cell ratio during the menstrual cycle immediately before, two cycles before, three cycles before, four cycles before, five cycles before, or six cycles before the day of receiving treatment; it is more preferable to perform determination of the Th1/Th2 cell ratio during the menstrual cycle immediately before or two cycles before the day of receiving treatment; and it is even more preferable to perform determination of the Th1/Th2 cell ratio during the menstrual cycle immediately before the day of receiving treatment. When the effect exerted by the menstrual cycle on the immune state is considered, it is preferable that the determination of the Th1/Th2 cell ratio is performed at relatively the same time point during the menstrual cycle in a normal person and a subject for administration of the medicine. It is also preferable that the determination of the Th1/Th2 cell ratio is performed during the low body temperature period (from the menstrual period to ovulation) of the menstrual cycle.

Without being particularly limited, more specifically, for example, the determination of the Th1/Th2 cell ratio in a subject with sterility can be carried out before the scheduled day of performing administration of the medicine, preferably at least during the period until 1 or 2 days before to 180 days before, more preferably during the period until 1 or 2 days before to 60 days before, and even more preferably during the period until 2 days before to 30 days before, the implantation of a fertilized ovum or a transplanted embryo. Without being particularly limited, more specifically, for example, the determination of the Th1/Th2 cell ratio in a subject who can have defective pregnancy conditions other than sterility (infertility and the like) can be carried out before the scheduled day of performing administration of the medicine, preferably during the period of from 0 days to 60 days, more preferably during the period of from 0 days to 30 days, even more preferably during the period of from 0 days to 20 days or from 0 days to 15 days, and particularly preferably during the period of from 0 days to 10 days, after confirmation of pregnancy.

The Th1/Th2 cell ratio may be the value of any tissue in the body of the subject for administration of the medicine; however, the ratio is preferably the value of peripheral blood.

Particularly Specific Examples of Subject for Administration of Medicine Infecundity A particularly preferred example of patient is a patient who meets the following conditions (1) and (2), more preferably a patient who also meets the condition (3), and even more preferably a patient who also meets the conditions (4) to (6).

(1) A patient of implantation disorder, in whom, among examples of severe infecundity without clearly acknowledged causes, even if embryo transplantation of a fertilized ovum (regardless of being a fresh embryo, a frozen embryo, an early stage embryo, or a blastocyst) having a clearly recognizable satisfactory shape, is carried out 4 or more times, scientific pregnancy (increased hCG) is not achieved.

(2) A patient at the age of below 40. (3) A patient having a high value of Th1/Th2 cell ratio, who is found when subjects are subjected to an immunological examination (screening) during the low body temperature period (from the menstrual period to ovulation) with satisfactory body condition before pregnancy.

(4) A patient who does not have any active infectious disease.

(5) A patient who does not have any sustained infectious disease of HBV, HCV, or HIV.

(6) A patient who does not have a medical history of hypersensitivity against tacrolimus component.

Infertilitas

A particularly preferred example of patient is a patient who meets the following conditions (1) and (2) (patients of infertilitas of unknown causes are included therein), and more preferably a patient who also meets the conditions (3) to (5).

(1) A patient of severe infertilitas in whom clear abnormal findings related to infertility are not recognized from a serological test.

(2) A patient of habitual abortion resistant to treatment (including anti-phosphorus antibody syndrome).

(3) A patient who does not have any active infectious disease.

(4) A patient who does not have any sustained infectious disease of HBV, HCV, or HIV.

(5) A patient who does not have a medical history of hypersensitivity against tacrolimus component.

Eclampsia

An example of a patient can meet at least one of the following criteria (1) and (2):

(1) A patient with a past history of both eclampsia and HELLP syndrome.

(2) A patient with a past history of miscarriage and/or stillbirth in her previous pregnancy.

HELLP syndrome can be managed or its onset can be prolonged by administering about 0.5-5 mg every day starting from the four weeks of gestation until the delivery.

General Terms

Without being particularly limited, patients who continuously receive administration of tacrolimus or a derivative thereof for a medical purpose other than amelioration of pregnancy conditions (for example, a patient who is continuously administered with tacrolimus after organ transplantation) may be excluded from the subject for administration of the medicine of the present invention.

Route of Administration/Method for Administration

The method for administration (route of administration) of the medicine of the present invention can be appropriately determined based on the age and condition of the subject for administration, the duration of treatment, and the like. Specifically, both oral administration and parenteral administration may be employed; however, oral administration is preferred (oral administration is employed in Examples). Examples of parenteral administration include methods such as administration by injection, administration using a suppository, and administration using a percutaneous absorption type preparation. Examples of the type of administration by injection include intramuscular injection, intraperitoneal injection, subcutaneous injection, intravenous injection, and local injection. Furthermore, the medicine of the present invention can be administered through various routes such as percutaneous, transnasal, transvaginal, and transrectal routes.

Dosage

The dosage of the medicine varies depending on the type of the disease, illness or condition of the patient who receives administration of the medicine, severity, results of various examinations, the type of the active ingredient of the medicine, and the like. Furthermore, the dosage of the medicine also varies depending on the age of the patient to be treated, the number of times of treatment according to the treatment method of the present invention, results of various examinations, and the like. For instance, from the viewpoint of the content of the active ingredient included in the medicine, the medicine of the present invention is administered at a dose that is lower than the dosage in the case in which the medicine is used as an immunosuppressant in the treatment for living donor organ transplantation and immune system diseases. For example, in a case in which the subject for administration of the medicine is a human being, without being particularly limited, the medicine is administered in an amount, as an amount of the active ingredient, preferably in the range of 0.5 to 5 mg or 1 to 5 mg, more preferably in the range of 0.5 to 4.5 mg or 1 to 4.5 mg, even more preferably in the range of 0.5 to 4 mg or 1 to 4 mg, still more preferably in the range of 0.5 to 3.5 mg or 1 to 3.5 mg, even more preferably in the range of 0.5 to 3 mg or 1 to 3 mg, and most preferably in the range of 1 to 2 mg, per day. Hereinafter, unless particularly stated otherwise, the description concerning the dosage of the medicine is applicable in the case in which the subject is a human being, and the dosage is disclosed as the amount of the active ingredient.

Furthermore, without being particularly limited, in the case of oral administration, the frequency of administration per day is preferably 1 to 4 times, more preferably 1 to 3 times, and even more preferably 1 to 2 times.

If necessary, the Th1/Th2 cell ratio described above (also see Examples) may be determined in advance, and the dosage may be determined based the value of the ratio. In regard to continuous administration for a certain period of during pregnancy and after delivery, including the treatment for infertility, the Th1/Th2 cell ratio may be measured at a constant interval during the duration of treatment, and the dosage may be determined based on the measurement results every time the cell ratio is measured anew.

As an example of determining the dosage based on the value of the Th1/Th2 cell ratio, in a case in which the Th1/Th2 cell ratio is 10 or higher, the medicine is administered in an amount, as an amount of the active ingredient, preferably in the range of 0.5 to 5 mg or 1 to 5 mg, more preferably in the range of 0.5 to 4.5 mg or 1 to 4.5 mg, even more preferably in the range of 0.5 to 4 mg to 1 to 4 mg, still more preferably in the range of 0.5 to 3.5 mg or 1 to 3.5 mg, even more preferably in the range of 0.5 to 3 mg or 1 to 3 mg, and most preferably in the range of 1 to 2 mg, per day. As another example, in a case in which the Th1/Th2 cell ratio is in the range of from 10 to 13, the medicine is administered in an amount, as an amount of the active ingredient, preferably in the range of 0.5 to 3 mg or 1 to 3 mg, more preferably in the range of 0.5 to 2 mg to 1 to 2 mg, and even more preferably in the range of 0.5 to 1 mg, per day. As another example, in a case in which the Th1/Th2 cell ratio is in the range of higher than 13 and 16 or lower (for example, 15.8 or less), the medicine is administered in an amount, as an amount of the active ingredient, preferably in the range of 0.5 to 4 mg or 1 to 4 mg, more preferably 0.5 to 3.5 mg or 1 to 3.5 mg, and even more preferably in the range of 1 to 3 mg or 1.5 to 2.5 mg, per day. As another example, in a case in which the Th1/Th2 cell ratio is 15 or higher (for example, in the case of being higher than 15.8), the medicine is administered in an amount, as an amount of the active ingredient, preferably in the range of 0.5 to 5 mg or 1 to 5 mg, more preferably in the range of 0.5 to 3.5 mg or 1 to 3.5 mg, and even more preferably in the range of 2 to 3.5 mg or 2.5 to 3.5 mg, per day.

The dosage of the medicine can be increased in accordance with the number of times of performing the amelioration method according to the present invention (number of times of pregnancy). For example, every time the number of times of treatments is traced during the treatment for sterility (an embodiment of amelioration), the dose per day is increased preferably by 0.5 to 3 mg (amount of the active ingredient; hereinafter, the same), more preferably by 0.5 to 2 mg, and even more preferably by 0.5 to 1 mg, from the dose at the time of treatment of the previous time. That is, with regard to the dose per day of the medicine that is administered from the beginning to the end of the first duration of treatment, the dose per day for the second duration of treatment that is carried out subsequently to the first duration of treatment, is increased by 0.5 to 3 mg. This is repeated every time for a single duration of treatment until pregnancy is established.

Regarding the number of times of treatments for the treatment of sterility (an embodiment of amelioration), preferably, repetition of 2 times to 5 times is tolerated, and more preferably, repetition of 2 times to 4 times is tolerated. In regard to the repetition of treatment, it is preferable that the dose per day at the end of the final duration of treatment does not exceed the dose that is preferable for the treatment method of the present invention (up to 5 mg as the amount of the active ingredient, per day).

Furthermore, in regard to the treatment of infertility (an embodiment of amelioration), during the gestation period, the Th1/Th2 cell ratio may be measured at a constant interval, and every time the Th1/Th2 cell ratio has increased, the dose per day may be increased preferably by 0.5 to 3 mg (amount of the active ingredient; hereinafter, the same), more preferably by 0.5 to 2 mg, and even more preferably by 0.5 to 1 mg, every time.

The dosage described above provides values that are applicable to women in general; however, when a woman has a body weight that is extremely far from the standard body weight (for example, a woman having a body weight of less than 45 kg or a woman having a body weight of more than 75 kg) is the subject, the dosage per kg of body weight may be determined by dividing the dosage by 60 (kg), and thereby the actual dosage may be adjusted according to the actual body weight of the subject.

In the case of using a medicine including rapamycin or a derivative thereof as the active ingredient, an appropriate dosage in accordance with the type of the active ingredient can be set; however, in addition to the embodiment of applying the above-mentioned dosage as an example, an embodiment of applying a dosage obtained by multiplying the above-mentioned dosage by ⅔ may also be employed. In the case of using a medicine including cyclosporin or a derivative thereof as the active ingredient, an appropriate dosage in accordance with the type of the active ingredient can be set; however, for example, an embodiment of applying a dose of 1,000 mg or less, and preferably 60 mg or less, per day as the amount of the active ingredient may also be employed.

Timing and Duration of Administration of Medicine

The timing and duration of the administration of the medicine of the present invention vary depending on the disease, illness or condition as an object of amelioration. In a case in which a human subject suffers from sterility, it is preferable that the medicine is administered at least for a period from preferably 1 or 2 days before to 60 days before, more preferably 2 to 30 days before, or even more preferably 2 to 15 days before the implantation of a fertilized ovum or a transplanted embryo into the endometrium, until preferably 0 to 100 days after, or more preferably 0 to 15 days after (0 to 1, 2, 3, 4, 5, 6, 7, 8, 9, 10, 11, 12, 13, 14, or 15 days after) the implantation. When the subject is a patient who has received a treatment of artificial insemination or in vitro fertilization, the administration of the medicine is carried out for a period from preferably 1 or 2 days to 60 days before, more preferably 2 to 30 days before, and even more preferably 2 to 15 days before sperm injection or embryo transplantation until preferably 0 to 100 days after, and more preferably 0 to 15 days after (0 to 1, 2, 3, 4, 5, 6, 7, 8, 9, 10, 11, 12, 13, 14 or 15 days after) sperm injection or embryo transplantation.

Furthermore, in a case in which a human subject suffers from infertility (pregnancy loss), it is preferable that the medicine is continuously administered preferably from the day of confirming establishment of pregnancy until after 200 days, more preferably from the day of confirming establishment of pregnancy until after 300 days, or even more preferably from the day of confirming establishment of pregnancy until the delivery.

In a case in which a human subject has a risk of having pregnancy complications (including pregnancy-induced hypertension syndrome), it is preferable that the medicine is continuously administered preferably from the day of confirming establishment of pregnancy until after 200 days, more preferably from the day of confirming establishment of pregnancy until after 300 days, even more preferably from the day of confirming establishment of pregnancy until the delivery, or most preferably from the day of confirming establishment of pregnancy to 60 days after the delivery.

Furthermore, the dose can also be appropriately modified at any stage of the first trimester, the second trimester, or the third trimester of pregnancy. For example, as the subject goes through each stage of the first trimester, the second trimester, and the third trimester of pregnancy and the gestation period described below, the dose of the medicine per day may be reduced stepwise by 0.5 to 1 mg. Alternatively, an embodiment of administering the medicine only during the first trimester of pregnancy and stopping administration from the second trimester may be employed; an embodiment of continuing administration until the second trimester of pregnancy but stopping administration from the third trimester may be employed; or an embodiment of administering the medicine only during the first trimester and the third trimester of pregnancy and pausing administration during the second trimester may also be employed.

Furthermore, the duration of continuous administration may also be regulated depending on whether the examination results for pregnancy conditions at each stage of pregnancy are satisfactory. From 100 days after the establishment of pregnancy, the mother's body enters a stable period of pregnancy. Therefore, the dose of the medicine is reduced as far as possible so long as sufficient therapeutic effects are obtained, and thereby the influence of adverse effects of the medicine on the mother's body and the fetus is suppressed to the minimum. Thus, the physical and burden on the subject for administration can be reduced to the minimum.

2. Method for Ameliorating Pregnancy Conditions

A method for ameliorating pregnancy conditions using the medicine according to the present invention (an embodiment thereof is a method for treating defective pregnancy conditions) is also within the scope of the present invention. The details of the method for ameliorating pregnancy conditions of the present invention are hereinafter explained.

The method for ameliorating pregnancy conditions according to an embodiment of the present invention includes a step of administering the medicine according to the present invention to a subject (administration step). The term amelioration of pregnancy conditions means that defective pregnancy conditions are ameliorated to a satisfactory state or a normal state, and this is a concept that also includes prevention of acquiring defective pregnancy conditions. Specific examples of the defective pregnancy conditions include sterility, infertility, and pregnancy complications such as pregnancy-induced hypertension syndrome. The disease, illness, and condition included in the concept of defective pregnancy conditions are as explained in the aforementioned section of (Subject for administration of medicine) in [1. Medicine (pharmaceutical composition)]. Regarding the active ingredient, the medicine to be administered contains a compound represented by General Formula (I) described above or a pharmaceutically acceptable salt thereof as an active ingredient, or contains cyclosporin, rapamycin, or a derivative thereof (including a pharmaceutically acceptable salt thereof) as active ingredients. Also in regard to the medicine according to the present invention, the matters explained in the aforementioned section [1. Medicine (pharmaceutical composition)] are included. The subject to which the therapeutic method of the present invention is applied is as explained in the section of (Subject for administration of medicine) in [1. Medicine (pharmaceutical composition)].

The therapeutic method of an embodiment of the present invention according to another embodiment may further include, in addition to the administration step, (1) a step of measuring the Th1/Th2 cell ratio, and/or (2) a step of performing artificial insemination (injection of sperms into the womb) or transplanting a fertilized ovum or an embryo obtained by in vitro fertilization into the endometrium. The various steps are explained in more detail below.

Administration Step

The administration step is a step of administering the medicine according to an aspect of the present invention to a subject.

When the method of the embodiment is a method for ameliorating (including a therapeutic method) sterility in a human subject, regarding the period for administration of the medicine in the administration step, it is preferable that the medicine is administered at least for a period from preferably 1 or 2 days to 60 days before, more preferably 2 to 30 days before, or even more preferably 2 to 15 days before the implantation of a fertilized ovum or a transplanted embryo into the endometrium until preferably 0 to 100 days after, or more preferably 0 to 15 days after, the implantation. When the human subject is a patient who has received treatment for artificial insemination or in vitro fertilization, administration is carried out for a period from preferably 1 or 2 days to 60 days before, more preferably 2 to 30 days before, or even more preferably 2 to 15 days before sperm injection or embryo transplantation, and until preferably 0 to 100 days after, or more preferably 0 to 15 days after spec injection or embryo transplantation.

When the method is a method for ameliorating (including a therapeutic method) infertility in a human subject, the period for administration of the medicine in the administration step is preferably from the day of confirming establishment of pregnancy until after 200 days, more preferably from the day of confirming establishment of pregnancy until after 300 days, or even more preferably from the day of confirming establishment of pregnancy until the delivery.

When the method is a method for ameliorating (also including prevention of) pregnancy complications such as pregnancy-induced hypertension syndrome in a human subject, the period for administration of the medicine in the administration step is preferably from the day of confirming establishment of pregnancy until after 200 days, more preferably from the day of confirming establishment of pregnancy until after 300 days, even more preferably from the day of confirming establishment of pregnancy until the delivery, or most preferably from the day of confirming establishment of pregnancy until 60 days after the delivery.

When the method is treating or managing HELLP syndrome or prolong the onset of HELLP syndrome, the medicine may be administered about 0.5-5 mg every day starting from about four weeks of gestation until the delivery.

Administration during the above-mentioned period may be continuous (that is, administered everyday during the period), or may be intermittent (that is, days without administration may be included during the period). More particularly, the description in (Timing and duration of administration of medicine) of [1. Medicine (pharmaceutical composition)] is applied. Specific examples of intermittent administration include an embodiment of administering the medicine with regularity of once in predetermined dates (1 day, 2 days, or 3 days), and an embodiment of administering the medicine one or more predetermined stoppage period(s) composed of a plurality of days.

The dosage is as described in the section of (Dosage) in [1. Medicine (pharmaceutical composition)].

Step of Measuring Th1/Th2 Cell Ratio

Furthermore, the method according to another embodiment of the present invention may further include a step of measuring the Th1/Th2 cell ratio. The Th1/Th2 cell ratio thus determined may also be used for the determination of the necessity of administration of the medicine to the subject, or the determination of the dosage of the medicine, as described in the section [1. Medicine (pharmaceutical composition)]. The step of measuring the Th1/Th2 cell ratio is carried out before the administration step. Here, the term "before the administration step" refers to the time between an administration and another administration during a single period of administration, and also refers to a time before the initial administration during a single period of administration (treatment period).

When the method of an embodiment of the present invention is a method for ameliorating sterility, the step of measuring the Th1/Th2 cell ratio can be carried out, for example, before the scheduled day of performing administration of the medicine, preferably during a period of from 1 or 2 days to 180 days before, more preferably a period of from 1 or 2 days to 60 days before, and even more preferably a period of from 2 days to 30 days before the implantation of a fertilized ovum or a transplanted embryo.

When the therapeutic method of an embodiment of the present invention is a therapeutic method for ameliorating defective pregnancy conditions other than sterility, including infertility and pregnancy complications such as pregnancy-induced hypertension syndrome, the step of measuring the Th1/Th2 cell ratio can be carried out before the scheduled day of performing administration of the medicine, preferably during a period of from 0 days to 60 days, more preferably a period of from 0 days to 30 days, even more preferably a period of from 0 days to 20 days or from 0 days to 15 days, or particularly preferably a period of from 0 days to 10 days after the confirmation of pregnancy.

Step of Performing Artificial Insemination or Transplanting Fertilized Ovum or Embryo Obtained by in Vitro Fertilization into Endometrium Upon applying the method for ameliorating pregnancy conditions using the medicine according to the present invention, the subject (including a human subject) may receive a treatment of artificial insemination (injection of sperms into the womb), or may receive a treatment of transplanting a fertilized ovum or an embryo obtained by in vitro fertilization into the endometrium. Ameliorating the pregnancy conditions related to a fertilized ovum or a transplanted embryo that has been implanted after receiving said treatment is a particularly preferred embodiment of the present invention. Specific methods for in vitro fertilization include methods such as IVF-ET and ICSI. IVF-ET is further classified into fresh embryo transplantation (fresh ET) of using a fresh embryo for transplantation and freeze-thaw embryo transplantation (FET) of using a frozen and thawed embryo that has been stored in a frozen state after collection for transplantation. Among them, FET is preferable. When the medicine of the present invention is administered, the efficiency of establishment of pregnancy and childbirth of a subject who has received these therapeutic methods can be increased, and the onset of pregnancy complications, etc. can also be suppressed.

However, the establishment of pregnancy in a subject with sterility or infertility may be based on spontaneous impregnation, and ameliorating the pregnancy conditions in spontaneous impregnation is also included in the scope of the present invention.

4. Other Embodiments

Furthermore, use of at least one compound selected from Compound (I) described above, rapamycin or a derivative thereof, cyclosporin or a derivative thereof, and pharmaceutically acceptable salts thereof, for the production of a medicine for ameliorating pregnancy states is also included in the scope of the present invention.

5. Summary

That is, the disclosure includes the following non-limiting embodiments.

1) A medicine for ameliorating pregnancy conditions, containing a compound represented by General Formula (I) described above (Compound (I)) or a pharmaceutically acceptable salt thereof as an active ingredient.

2) The medicine according to 1), wherein the compound is tacrolimus or a pharmaceutically acceptable salt thereof.

3) The medicine according to 1) or 2), which ameliorates defective pregnancy conditions attributed to immunological abnormalities.

4) The medicine according to any one of 1) to 3), which ameliorates at least one type of defective pregnancy condition selected from the group consisting of sterility, infertility, and pregnancy-induced hypertension syndrome.

5) The medicine according to 4), wherein the aforementioned sterility and infertility are accompanied by an autoimmune disease.

6) The medicine according to 5), wherein the autoimmune disease is anti-phospholipid antibody syndrome.

7) The medicine according to any one of 1) to 6), wherein the medicine is administered to a subject of treatment with an amount of 5 mg or less per day of the aforementioned active ingredient.

8) The medicine according to 7), wherein the amount of the aforementioned active ingredient is in the range of from 1 mg to 3 mg per day.

9) The medicine according to any one of 1) to 8), wherein the medicine is administered to a subject who has an increased Th1/Th2 cell ratio compared to a healthy person.

10) The medicine according to any one of 1) to 9), wherein the medicine is administered to a subject who has received to transplantation of an embryo obtained by in vitro fertilization.

11) The medicine according to any one of 1) to 9), wherein the medicine is administered at least during a period from 1 or 2 days before the implantation of a fertilized ovum or a transplanted embryo into the endometrium, to 0 days after the implantation in a case in which the medicine is intended for sterility as a defective pregnancy condition; and the medicine is administered at least for a period from the establishment to the $200^{th}$ day of pregnancy in a case in which the medicine is intended for a defective pregnancy condition other than sterility.

12) A method for ameliorating a pregnancy condition, including a step of administering a medicine containing aforementioned compound (I) or a pharmaceutically acceptable salt thereof as an active ingredient for ameliorating pregnancy conditions, wherein the medicine includes.

13) The method according to 12), wherein the aforementioned medicine is administered by any one form or embodiment according to 2) to 11).

Example 1

Objective

We, the inventors, evaluated the clinical efficacy of immunosuppressive treatment with tacrolimus for repeated implantation failure (RIF) patients who have elevated in T helper (Th) 1/Th2 cytokine producing cell ratios (Th1/Th2 cell ratio).

Method of Study:

This was a prospective cohort study of treatment for RIF patients (n=42) with elevated peripheral blood Th1 ($CD4^+$/$IFN-\gamma^+$)/Th2 ($CD4^+$/$IL-4^+$) cell ratios at the Sugiyama clinic between November 2011 and October 2013. Twenty-five patients were treated with tacrolimus (treatment group) and 17 received no treatment (control group).

Treatment group continuously received tacrolimus from two days before embryo transfer until the day of the pregnancy test, for a total of 16 days. The daily dose of tacrolimus (1-3 mg) was determined based on the degree of the Th1/Th2 cell ratio.

Results:

The clinical pregnancy rate of the treatment group was 64.0%, which was significantly higher than that of the control group (0%) ($P<0.0001$). In the treatment group, the miscarriage rate was 6.3%, the live birth rate was 60.0% ($P<0.0001$). There was no significant side effect from tacrolimus in treatment group. No one developed obstetrical complications during pregnancy.

Conclusion:

An immunosuppressive treatment using tacrolimus improved pregnancy outcome of repeated implantation failure patients with elevated Th1/Th2 cell ratios.

Introduction

Incidence of in-vitro fertilization (IVF) and embryo transfer (ET) has been soared recent years world-wide.[1] This was accompanied by an increase in number of women with multiple IVF failures, including repeated implantation failures (RIF). When conducting IVF/ET, an embryo is transferred to the uterine cavity between 2 to 5 days after fertilization. Pregnancy is established when an embryo, which is so to speak a semi-allograft, is successfully implanted to maternal decidua with an establishment of maternal immune tolerance.[2] The establishment of proper immune responses at the time of implantation is a key for successful implantation. Hence, immune etiology may play a key role in RIF after IVF/ET.

T helper (Th) 1 and Th2 cells play important roles in immune responses, such as immune rejection or tolerance.[3] There is a general agreement that pregnancy is associated with Th2 dominance, and Th1 immune response is associated with embryonic rejection.[4,5] An underling mechanism of embryo rejection is considered to be similar to an allograft rejection.[6] A transferred embryo during IVF/ET may fail to implant due to the similar immunological reaction involved in allograft rejection.

In the past decades the graft survival rate has been dramatically improved.[7] This success can be attributed to the development of new immunosuppressive agents. Tacrolimus (Prograf®, Astellas Pharma, Tokyo) is one of the major immune-suppressive agents that have been utilized after allogeneic organ transplantation to reduce the allo reactivity of a recipient's immune system, thereby lowering the risk of organ rejection.[8] Tacrolimus has been reported to suppress the immunological rejection of an allo-graft and promote its survival by inhibiting lymphocyte proliferation induced by allo-antigens, cytotoxic T cell generation, expression of IL-2 receptor and the production of T cell derived soluble mediators such as IL-2 and IFN-$\gamma$.[9] Tacrolimus has been reported to effectively control graft versus host disease or other immunological disorder such as rheumatoid arthritis,[10,11] although different subsets of T-lymphocytes are associated with these conditions. Women with RIF have increased Th1 immune responses with increased peripheral blood Th1/Th2 cell ratio.[4] Therefore, an immune-suppressive agent, such as tacrolimus might improve implantation rates and pregnancy outcome in women who have a history of RIF after ART cycles, particularly with increased Th1 immunity response. In this study, we investigated the clinical efficacy of tacrolimus for women with RIF and an elevated peripheral blood Th1/Th2 cell ratio.

Materials and Methods

Study Population

A total of 81 patients with a history of 5 or more RIF after IVF/ET cycles were consecutively enrolled in the study at the division of Reproductive Medicine, the Sugiyama clinic, Tokyo, Japan, between November 2011 and February 2014. This study was approved by the Institutional Review Board of the Sugiyama Clinic. A signed informed consent form was obtained from all patients prior to entering the study.

Study patients were selected if they were eligible for IVF/ET, and had a history of 5 or more failed IVF/ET cycles with morphologically and developmentally good-quality embryos into an adequately prepared endometrium (endometrial thickness ≤8 mm). Study patients were assessed by transvaginal ultrasound, hysterosalpingography, and hysteroscopy before the index ART cycle. None of the participants had submucosal fibroids, endometrial polyps, intrauterine adhesions, congenital anomalies of uterus or hydrosalpinges. In addition, none of the women had any history of autoimmune disease. Pregnant women or women with chronic medical or inflammatory conditions were excluded. Women who miscarried in a former IVF cycle or had IVF cycles, or received vaccination in 3 months were excluded in the study. Women with acquired or inherited thrombophilia were also excluded in this study.

Blood was drawn between cycle day (CD) 5 and 10 prior to the index ART cycle for the evaluation of a baseline value of Th1/Th2 cell ratios. Forty-two patients had elevated Th1/Th2 cell ratio (≥10.3) and 39 had normal Th1/Th2 cell ratio (<10.3). Normal ranges for Th1/Th2 cell ratios were established using 28 women who had a history of normal delivery by either natural conception or artificial insemination with husband sperm. Blood was drawn between CD5 and CD10 of the menstrual cycle. A Th1/Th2 cell ratio equal to 10.3 or above was classified as an elevated Th1/Th2 cell ratio, which was determined by the mean plus one standard deviation of Th1/Th2 cell ratio levels.

Analyses of the Th1 and Th2 Cells

For the evaluation of a baseline value of Th1/Th2 cell ratios, total 10 ml of venous blood was obtained. Th1 and Th2 cells were determined by detecting the intracellular interferon (IFN)-$\gamma$ and IL-4 production.

The specific staining of lymphocytes was performed by incubating whole blood with anti-CD4-PC5 or anti-CD8-PC5-conjugated monoclonal antibodies (mAbs) (Beckman Coulter, Fullerton, Calif., USA). The red blood cells (RBCS) were then removed by lysis (FACS Lysing solution; Becton Dickinson, BD Biosciences, Franklin Lake. N.J., USA) and the lymphocytes were analyzed using flow cytometry (FACSCalibur; Becton Dickson). After surface staining of the activated whole blood samples with anti-CD4-PC5 conjugated mAbs, RBC lysis and specific intracellular staining using FastImmune™ IFN-$\gamma$-FITC/IL-4-PE (Becton Dickinson) were subsequently performed according to the manufacturer's instructions. Th1 cells were defined as $CD4^+$ lymphocytes with intracellular IFN-$\gamma$ but without IL-4. Th2 cells were detected as $CD4^+$ lymphocytes with intracellular IL-4 but without IFN-$\gamma$. The ratio of IFN-$\gamma$ to IL-4 positive Th cells was expressed as the Th1/Th2 cell ratio.

Tacrolimus (Prograf®) Treatment

In 42 patients with elevated Th1/Th2 cytokine ratios (equal or above 10.3), 25 of them were treated with tacrolimus (Prograf®, Astellas Pharma, Tokyo; treatment group), and the others (n=17) were not treated (control group) during the index IVF/ET cycles. The patients in the treatment group began tacrolimus two days prior to ET and continued until the day of pregnancy test, for a total of 16 days. The daily dosage of tacrolimus was 1 to 3 mg depending on the degree of Th1/Th2 cell ratio elevation; patients (n=12) with mildly increased Th1/Th2 cell ratio (≥10.3 and <13.0) were treated with 1 mg of tacrolimus, daily. Patients (n=8) with moderately increased Th1/Th2 cell ratio (≥13.0 and <15.8) were treated with 2 mg of tacrolimus daily. Patients (n=5) with highly increased Th1/Th2 cell ratio (≥15.8) were treated with 3 mg of tacrolimus daily.

IVF-ET Treatment

Ovarian stimulation and the oocyte pick-up (OPU) were performed as usual according to our previous report.[12] Our mild stimulation protocol was as follows: patients took 50 mg of clomiphene citrate (Serophen®, Merck Serono, Tokyo) per day for 5 days between days 3 and 7 of the menstrual cycle, and 225 International Units (IU) of rec- FSH (Gonal-F®, Merk Serono, Tokyo) were administered on days 4, 6 and 8 of the menstrual cycle. On day 10, when the dominant follicles reached ≥17 mm in diameter, either 10,000 IU of human chorionic gonadotropin (hCG; Gonadotropin, Mochida, Tokyo) was injected, or 300 µg of buserelin acetate (Buserecur, Fuji Pharma, Tokyo) was administered nasally, and OPU was performed 35 hours later. Additional rec-FSH (150 IU per a day) was administered as needed, based on follicular growth. Either intracytoplasmic sperm injection (ICSI) or conventional co-culture was used depending on the semen parameters.

Embryos were placed to the patient's uterus transcervically using a soft catheter (Kitazato ET catheter, Kitazato Supply, Shizuoka, Japan). In all patients, either one or two embryos were transferred. Fresh ET was performed on day 3. Any remaining embryos were cryopreserved using vitrification.[13] On the day of ET and 5 days after ET, 125 mg of hydroxyprogesterone caproate (Progestone Depot-S, Fuji Pharma, Tokyo) was injected for luteal support. Chlonnadinone acetate (Lutoral®, Shionogi, Osaka) was administered orally for 14 days after ET. For the frozen-thawed ET (FET) cycle, endometrial preparation was used either natural ovulatory cycle or hormone replacement cycle. Using natural ovulatory cycle the day of ET was defined as 3 days after the ovulation. The same luteal support as in the fresh ET cycle was administered. Using hormonal replacement cycle (HRC), the uterine endometrium was prepared for ET using conjugated estrogens (Premarin 0.625 mg, Wyeth, Tokyo, Japan) and transdermal estradiol (Estrana TAPE 0.72 mg, Hisamitsu Pharmaceutical, Tokyo, Japan). These treatments were administered from the 3rd day of the menstrual cycle or the 1st day without bleeding until the day of the urinary pregnancy test. Administration of progesterone (100 mg in oil; Progestone Depot-S, Fuji Pharmaceutical, Tokyo, Japan) was initiated on the 12th day of the menstrual cycle. Three days after the initiation of progesterone treatment, embryos were thawed and those that had survived were transferred.[14]

All patients received a transfer of one or two morphologically good-quality embryos (MGEs) 3 days after oocyte retrieval. For frozen embryo cycle, 3 day old frozen-thawed embryos were transferred 3 days after ovulation in natural ovulatory cycle or 3 days after progesterone administration in HRC. MGEs were defined as having 7 or more blastomeres and possessing less than 10% of fragmentation 3 days after oocyte retrieval.[13] Pregnancy test was done 14 days after ET. A clinical pregnancy was recognized when the development of a gestational sac was detected by transvaginal ultrasound 21 days after ET. An ongoing pregnancy was recognized when a normal fetus was seen by transvaginal ultrasound at 12th week of gestation. The primary and secondary endpoints of this study were clinical pregnancy and delivery of a live born infant, respectively.

Statistical Analysis

A statistical analysis was performed using StatView, version 5 (SAS Institute Inc., Cary, N.C.). Continuous variables were analyzed by Wilcoxon signed rank test. Categorical variables were analyzed by $\chi^2$ analysis or Fisher's exact test as indicated. A probability of <0.05 was considered to be statistically different.

Results

Study Population

Age, obstetrical and infertility histories of the study and control groups are not different between the treatment group and controls (Table 1). The average age of the treatment group was 36.2±2.5 (mean±SD) years, which was comparable to that of control (36.1±4.1). Indications for assisted reproductive technology (ART) treatment of both groups were comparable. About one-fourth of the patients in the treatment group had a history of a positive pregnancy test, but none delivered a live born infant. The same trend was seen in the control group. The mean numbers and standard deviation (SD) of previous ET attempts, transferred embryos and transferred MGEs in the treatment group were 5.8±2.9, 8.6±5.8, and 5.0±2.1, respectively, and these were not significantly different from those in the control group (5.9±2.7, 7.4±3.4 and 4.9±2.0, respectively).

Th441/Th2 Cell Ratios

The results of the analyses of the Th1 and Th2 cells are also shown in table 1. The percentages of IFN-γ producing CD4+T lymphocytes (Th1) in the treatment and control groups were 27.7±9.4 and 26.7±7.3 (mean±S.D.) respectively, which revealed no significant differences. The percentages of IL-4 producing CD4+ T lymphocytes (Th2) in the treatment and control groups were 1.8±0.6 and 1.7±0.6 respectively, which was not significantly different. The Th1/Th2 cell ratio in the treatment group was 16.1±7.0, which was similar to that in the control group (16.7±5.2).

Treatment Outcome

The ART outcomes in both groups are summarized in table 2. The numbers of the transferred embryos per cycle in the treatment and control groups were 1.4±0.5 and 1.4±0.5, respectively (P=NS). The percentage of MGEs was 68.9% in the treatment group, which was comparable to that in the control group (70.8%). No one achieved a pregnancy in the control group and 16 patients out of 25 (64%) in the treatment group had a positive pregnancy test and progressed to clinical pregnancies with tacrolimus treatment. There was no biochemical loss and the implantation rate was 45.7% (16/35). The number of patients treated with 1 mg, 2 mg, or 3 mg of tracrolimus were 12, 8, and 5, respectively (table 3). The clinical pregnancy and live birth rates in the patients treated with 1 mg of tacrolimus were 83.3 and 83.3%, respectively, and these rates in the patients with 2 mg and 3 mg of tacrolimus were 50.0 and 37.5%, and 40.0 and 40.0%, respectively (Table 3).

Among the pregnant patients in the treatment group, only one experienced a miscarriage (6.3%) at 10 weeks gestation. Total fifteen healthy babies were born with tacrolimus treatment and the live birth rate in the treatment group was 60.0%. Obstetrical outcome of the newborns were as follows; birth weight (mean±SD) was 2,995±400 g, mean gestational days to delivery was 279.5±10.6, APGAR scores of 1 and 5 minutes after birth were 8.3±0.5 and 9.2±0.5, respectively, and 6 babies were delivered by Caesarian section and 9 were born by vaginal delivery (Table 4).

With tacrolimus treatment, twelve of 16 women (75%) who received frozen—thawed ET and 4 of 9 (44.4%) women with fresh ET become pregnant. Frozen-thawed ET cycle had a higher success rate than fresh IVF-ET cycle however, it did not reach statistical significance. Twelve of 16 women (75%) with FET and 3 of 9 (33.3%) women with fresh ET have delivered a live born infant. There is a trend of increased success rate in FET cycle as compared with fresh ET cycle in RIF patients with tacrolimus treatment (P<0.1).

Discussion

Repeated implantation failures (RIF) is often determined when embryos of good quality fail to implant following at least 3 consecutive IVF attempts, in which 1-2 embryos of high grade quality are transferred in each cycle.[15] However there is no general consensus for a definition yet. Implantation involves maternal immune system and many mediators such as cytokines, chemokines and various growth factors from an embryo and endometrium. Hence, stratifying patients only based on their infertility history, such as RIF may not be adequate for further evaluation and treatment. A recent review of endometrial receptivity report that there is no single biomarker which is specific for endometrial receptivity.[16] Although we measured endometrial thickness in this study as a standard infertility work up, objective diagnosis of endometrial receptivity is seemingly remote. The same may hold true for immunological factors, since only Th1/Th2 cell ratios are investigated in this study.

The treatment modalities for RIF patients with Th1/Th2 elevation have been previously reported. High-dose intravenous gammaglobulin G (IVIG) has been reported to be effective in women with repeated IVF and implantation failures.[17-19] IVIg reduces Th1/Th2 lymphocyte ratio in peripheral blood, which confirms a significance of Th1/Th2 immune regulation in implantation and maintenance of pregnancy.[17] Etanercept (Enbrel®), recombinant human TNF receptor [p75]:Fc fusion protein, has been reported to be effective in RIF patients who had an elevated peripheral blood Th1/Th2 ratio.[20] A recent publication detailing the use of IVIg and adalimumab (Humira™), which is a recombinant human IgG1 monoclonal antibody specific for TNF, showed improved pregnancy rates in RIF patients accompanied by Th1/Th2 elevation.[21] However, the safety of anti-TNF drugs, such as etanercept or adalimumab has not been established yet for either infertile or pregnant women.[22] Since tacrolimus has accumulated pregnancy safety data from transplant populations, in this study, we investigated if tacrolimus is suitable to regulate immunological responses and improve reproductive outcomes in women who had an extreme number of RIF (5 or more) after IVF cycles.

According to a previous report, a significant proportion of RIF patients have a dysregulated cellular immune effector mechanism[4,23] and an increased Th1 cytokine response was reported in women with RIF during their failed ART cycle.[24] In this study, 51.9% of women with RIF (≥5) had increased Th1/Th2 cell ratios particularly, when IL-4 and IFN-γ producing T cells were investigated. This was consistent with previous studies.[4,23]

Presence of Th1 immunity to semi-allogeneic embryo mirrors a graft rejection process during organ transplantation. Immunosuppressive drugs, such as tacrolimus are often prescribed for the recipients of an allogeneic organ transplant in order to reduce the risk of organ rejection.

Tacrolimus inhibits both T-lymphocyte signal transduction and IL-2 transcription.[20] In this study, Th1 shift was detected by measuring CD4+/IFN-γ and CD4+/IL-4 positive cell ratios. It has been reported that supra-physiological dose of IFN-γ induces peri-implantation failures in animal model by decreasing Treg and Th17 cells locally at implantation site.[25] Additionally, insulin-like growth factor binding protein 7 (IGFBP7) can lead to IFN-γ up-regulation with concurrent down regulation of IL-4 and IL-10, which lead to implantation failures in mice model.[26] Contrarily, IFN-γ induces appropriate arterial modifications at the implantation site.[27] Therefore, adequate expression and regulation of IFN-γ plays a key role in successful implantation and pregnancy. Considering dose dependent contradictory biological effects of IFN-γ, tracrolimus dose was determined based on Th1/Th2 cell ratio of women with RIF in this study. In addition, tacrolimus dose for study population was ranged 20-60% of prophylactic renal transplant schedule (0.1 mg/kg/day). All patients tolerated tacrolimus treatment well and no one reported side effect while on tacrolimus treatment. However, this observation should be carefully interpreted since the study size is small.

Tacrolimus has been utilized throughout pregnancy for women who have received an allogeneic organ transplant, and many female recipients have given birth while taking tacrolium.[28] Tacrolimus reduces peptidyl-prolyl isomerase activity by binding to the immunophilin FKBP12 (FK506 binding protein) creating a new complex. This FKBP12-FK506 complex interacts with and inhibits calcineurin thus inhibiting both T-lymphocyte signal transduction and IL-2 transcription.[29] Although this activity is similar to cyclosporin, studies have shown that the incidence of acute rejection is reduced by tacrolimus use over cyclosporin.[30] The effects on short-term immunosuppression and graft survival in patients are found to be similar between the two drugs, however, tacrolimus results in a more favorable lipid profile which may have important long-term implications given the prognostic influence of rejection on graft survival.[31]

Tacrolimus is classified as class C drug by the FDA pregnancy category. When considering RIF is not a life-threatening disease, class C drug application for women undergoing IVF cycle should be determined after careful benefit risk assessment. The safety of tacrolimus for both mother and fetus/baby during pregnancy has been well established in many reports of female transplant recipients who achieved a post-transplant pregnancy.[8,32] In 236 babies born from the kidney transplant recipients with tacrolimus exposure during pregnancy, the still born rate was 2% and the neonatal death rate was 2%.[33] Other reported obstetrical complications were preeclampsia 32%, diabetes during pregnancy 8%, hypertension 56%, infection 22%, and spontaneous abortion 26%.[33] In the present study, 60% (n=15) of the RIF patients with a Th1/Th2 elevation could achieve pregnancy and delivered a live born infant. No one had obstetrical complication and only one baby showed transient tachypnea of newborn. Differences in obstetrical outcomes between our study population and the renal transplant population could be related to the differences in general health status of the study population, dosage of tacrolimus and a duration of drug exposure. These patients could not achieve pregnancy prior even after ET of 5 MGEs.

Tacrolimus treatment significantly increased implantation rate, clinical pregnancy rate and live birth rate in women with RIF and elevated Th1/Th2 cell ratios. According to our data, the benefit of tacrolimus treatment during implantation period overweighs the risk to the developing fetus. Evaluation of Th1/Th2 cell ratio can be utilized as a biomarker for a selection of women with RIF, who will respond immune suppression treatment by tacrolimus and have successful reproductive outcome.

In this study, patients who had FET had higher success rate (75%) than fresh ET (33.3%) while on tacrolimus treatment. Recently, freeze-all strategies have been rapidly adopted by IVF centers since more receptive endometrium is expected in FET cycle, increased health of children born from the frozen-thawed embryos compared with those from fresh ET cycle, and increased success rates of FET that now almost equal the success rates of fresh ET.[27] Per 2011 CDC report, live birth rate of fresh ET cycle was 40% and FET was 39% for women under the age of 35 years.[33] In this study, despite of higher age of study population (mean age 36), FET success rate was 75% which was 1.9 times higher than reported success rate (39%) of women under 35.[27] Therefor, FET cycle with tacrolimus treatment can be applicable in RIF patients with advanced age group (>35). High clinical pregnancy rate of FET cycle may be resulted from a combined effect of Th1 immune regulation by Tacrolimus and more receptive endometrium by FET cycle. This study, however, has a limitation, since this is not a randomized controlled trial and a sample size is small. Moreover, endometrial changes or peripheral immune responses after tacrolimus treatment were not evaluated thoroughly. Further study is needed for tacrolimus effect on systematic immune responses and endometrial receptivity. In conclusion, an immunosuppressive treatment using tacrolimus improved pregnancy outcomes in RIF patients with elevated Th1/Th2 ratios. Further investigation, taking into account of Th17 and T regulatory cells, and endometrial receptivity is needed in considerable detail. Conclusively, this study indicates tacrolimus treatment significantly increases clinical pregnancy rate and live birth rate in RIF patients with shifted Th1 immune responses without increased maternal severe complications.

EXAMPLES

TABLE 1

Age obstetrical and infertility histories and clinical characteristics of women with repeated implantation failures (5 or more) and elevated Th1/Th2 ratios who were treated with tacrolimus (treatment group) and without tacrolimus (control group).

| Characteristics | Treatment group (n = 25) | Control group (n = 17) | P value |
|---|---|---|---|
| Age (years) | 36.2 ± 2.5 | 36.1 ± 4.1 | ns |
| Body mass index (Kg/m$^2$)$^a$ | 20.2 ± 1.4 | 20.4 ± 1.3 | ns |
| Indications for ART$^a$, % (n) | | | |
| Unexplained infertility | 80.0 (20) | 100 (17) | |
| Male infertility | 16.0 (4) | 0 | |
| Tubal infertility | 4.0 (1) | 0 | |
| Previous pregnancy history, % (n) | | | ns |
| No | 72.0 (18) | 64.7 (11) | |
| Yes | 28.0 (7) | 35.3 (6) | |
| Obstetrical history, % (n) | | | ns |
| Gravidity ≥ 1 | 28.0 (7) | 35.3 (6) | |
| Parity ≥ 1 | 0 (0) | 0 (0) | |
| SAB$^b$ ≥ 1 | 28.0 (7) | 35.3 (6) | |
| Previous embryo transfer history | | | |
| Number of failed embryo transfer cycle (n) | 5.8 ± 2.9 | 5.9 ± 2.7 | ns |
| Total number of transferred embryos (n) | 8.6 ± 5.8 | 7.4 ± 3.4 | ns |
| Total number of transferred MGE$^c$ (n)s | 5.0 ± 2.1 | 4.9 ± 2.0 | ns |
| Analyses of the Th1 and Th2 cells | | | |
| Th1 cells$^d$ (%) | 27.7 ± 9.4 | 26.7 ± 7.3 | ns |
| Th2 cells$^e$ (%) | 1.8 ± 0.6 | 1.7 ± 0.6 | ns |
| Th1/Th2 ratio | 16.1 ± 7.0 | 16.7 ± 5.2 | ns |

Women who miscarried in a former IVF cycle or had IVF cycles, or received vaccination in 3 months were exhaled in the study.
Values are mean ± standard deviation unless otherwise specified.
$^a$ART; assisted reproductive technology
$^b$SAB; spontaneous abortion. Women who miscarried within 3 months from prior IVF cycle were excluded from the study.
$^c$MGEs; morphologically good-quality embryos
$^d$Th1 cell; Interferon gamma producing T helper cell (CD3$^+$/4$^+$/IFN-γ$^+$)
$^e$Th2 cell; IL-4 producing T helper cell (CD3$^+$/4$^+$/IL-4$^+$)

Table 1 shows the age, obstetrical history, infertility history, and clinical characteristics of women with repeated implantation failures (5 or more times) and an elevated Th1/Th2 cell ratios, who were treated with tacrolimus (treatment group), and who were not treated (control group). In the table, "Body mass index" means BMI, "Unexplained infertility" means sterility of unknown causes, "Male infertility" means male sterility, and "Tubal infertility" means tubal sterility. "Previous pregnancy history" means the presence (Yes) or absence (No) of a pregnancy history in the past; "Obstetrical history" means a history of childbirth (Gravidity=reproductive history, Parity=birth history, SAB=spontaneous miscarriage); "Previous embryo transfer history" means a history of embryo transplantation in the past; "Number of failed embryo transfer cycle (n)" means the number of failed embryo transplantation cycles; "Total number of transferred embryos (n)" means the total number of transplanted embryos; and "Total number of transferred MGEs (n)" means the total number of transplanted MGEs. Th1/Th2 ratio refers to the Th1/Th2 cell ratio.

TABLE 2

Reproductive outcomes of women with repeated implantation failures who were treated with tacrolimus (treatment group) and without treatment (control group).

| | Treatment group (n = 25) | Control group (n = 17) | P value |
|---|---|---|---|
| Number of transferred cycles, n | 25 | 17 | — |
| Number of transferred embryos per cycle | 1.4 ± 0.5 | 1.4 ± 0.5 | ns |
| Frozen-thawed embryo transfer, n | 16 | 11 | — |
| Fresh embryo transfer, n | 9 | 6 | — |
| Percentage of MGEs$^a$ (%) | 68.9 | 70.8 | ns |
| Endometrial lining (mm) | 10.8 ± 1.4 | 11.0 ± 1.9 | ns |
| Positive hCG (%) | 64.0 | 0 | P < 0.0001 |
| Implantation rate (%) | 45.7 | 0 | P < 0.0001 |
| Biochemical pregnancy rate (%) | 0 | 0 | — |
| Clinical pregnancy (n) | 16 | 0 | — |
| Clinical pregnancy of fresh ET (%) | 44.4 | 0 | ns |
| Clinical pregnancy of cryo-thaw ET (%) | 75.0 | 0 | P < 0.0001 |
| Clinical pregnancy rate per ET (%) | 64.0 | 0 | P < 0.0001 |
| Spontaneous abortion rate (%) | 6.3 | | ns |
| Live birth (n) | 15 | 0 | — |
| Live birth rate of fresh ET (%) | 33.3 | 0 | ns |
| Live birth rate of thawed ET (%) | 75.0 | 0 | P < 0.0001 |
| Live birth rate (%) | 60.0 | 0 | P < 0.0001 |
| Live birth (n) | 15 | 0 | — |

RIF; repeated implantation failure,
$^a$MGEs: morphologically good embryo
Values are mean ± standard deviation unless otherwise specified.

Table 2 shows the birth outcome of women with repeated implantation failures (RIF), who were treated with tacrolimus (treatment group) and who were not treated (control group). In the table, "Number of transferred cycles" means the number of transplantation cycles; "Number of transferred embryos per cycle" means the number of transplanted embryos per cycle; "Frozen-thawed embryo transfer, n" means the number of transplantations of frozen and thawed embryos; "Fresh embryo transfer, n" means the number of transplantations of fresh embryos; "Percentage of MGEs" means the proportion (%) of MGEs; "Endometrial lining" means the thickness of the endometrium; "Positive hCG (%)" means the proportion (%) of positive hCG; "Implantation rate (%)" means the ratio of implantation (%); "Biochemical pregnancy rate (%)" means the biochemical pregnancy ratio (%); "Clinical pregnancy (n)" means the number of individuals who have achieved clinical pregnancy; "Clinical pregnancy of fresh ET (%)" means the clinical pregnancy ratio (%) with fresh ET; "Clinical pregnancy rate per ET (%)" means the clinical pregnancy ratio (%) per round of ET; "Spontaneous abortion rate" means the ratio of spontaneous miscarriage (%); "Live birth (n)" means the number of live births; "Live birth rate of fresh ET (%)" means the live birth ratio (%) with fresh ET; "Live birth rate of thawed ET (%)" means the live birth ratio (%) with frozen-thawed ET; and "Live birth rate (%)" means the live birth ratio (%).

TABLE 3

Reproductive outcomes of women with repeated implantation failures who were treated with various dosage of tacrolimus (treatment group).

| | Treatment group (n = 25) | Treatment dosage |
|---|---|---|
| Number of patients treated with | | |
| 1 mg of tacrolimus, n | 12 | 518 |
| 2 mg of tacrolimus, n | 8 | 519 |
| 3 mg of tacrolimus, n | 5 | 520 |
| Clinical pregnancy (n) | 16 | |
| with 1 mg of tacrolimus (%) | 83.3 | |
| With 2 mg of tacrolimus | 50.0 | |
| with 3 mg of tacrolimus | 40.0 | |
| Live birth (n) | 15 | |
| with 1 mg of tacrolimus (%) | 83.3 | |
| With 2 mg of tacrolimus | 37.5 | |
| with 3 mg of tacrolimus | 40.0 | |

Table 3 shows the birth outcome of women with repeated implantation failure (RIF) who were treated with various treatment dosages of tacrolimus (treatment group). In the table, "Number of patients treated with" means the number of patients who were treated with a predetermined dose; "Clinical pregnancy (n)" means the number of individuals who have achieved clinical pregnancy; and "Live birth (n)" means the number of live births. The dosage of tacrolimus is 1 mg, 2 mg, or 3 mg.

TABLE 4

Obstetrical and neonatal outcome of women with multiple implantation failures (5 or more) who were treated with tacrorimus.

| | |
|---|---|
| Number of newborns (n) | 15 |
| Mode of delivery | |
| vaginal delivery (n) | 9 |
| Cesarean section (n) | 6 |
| Gestational days to delivery (days) | 279.5 ± 10.6 |
| Birth weight (gm)$^a$ | 3,021 ± 371 |
| Height (cm)$^a$ | 50.9 ± 0.9 |
| Sex of newborn, boy/girl (n/n) | 7/8 |
| APGAR score at 1 minutes after birth | 8.3 ± 0.5 |
| APGAR score at 5 minutes after birth | 9.2 ± 0.6 |
| Umbilical cord gas analysis (pH) | 7.2 ± 0.05 |
| Umbilical cord length (cm) | 56.2 ± 12.2 |
| Obstetrical complications (n) | 0 |
| Neonatal complications (n) | One case of TTN 1 case |

Values are mean ± standard deviation unless otherwise specified.
$^a$TTN; transient tachypnea of newborn.

Table 4 shows the outcome of births and newborn baby births of women with multiple implantation failures (5 or more times), who were treated with tacrolimus. In the table, "Number of newborns (n)" means the number of newborn babies; "Mode of delivery" means whether the mode of delivery is vaginal delivery or Cesarean section; "Gestational days to delivery (days)" means the number of gestational days; "Birth weight" means the body weight at the time of birth; "Height" means the height at the time of birth; "Sex of newborn" means whether the gender of the newborn baby is male (boy) or female (girl); "APGAR score at 1 (or 5) minutes after birth" means the APGAR score obtained one minute (5 minutes) after birth; "Umbilical cord gas analysis (pH)" means the result of a gas analysis (pH) of the umbilical cord; "Umbilical cord length" means the length of the umbilical cord; "Obstetrical complications (n)" means the number of individuals with onset of pregnancy complications; and "Neonatal complications (n)" means that there were instances of onset of transient tachypnea of the newborn (TNN).

LIST OF REFERENCE DOCUMENTS

Document 1: Sunderam S, Kissin D M, Crawford S, Anderson J E, Folder S G, Jamieson D J, Barifield W D: MMWR Surveill Summ 2013; 62: 1-24.
Document 2: Schjenken J E, Tolosa J M, Paul J W, Clifton V L, Smith R: Croatia, INTECH, 2012, pp 211-242.
Document 3: aito S, Nakashima A, Shima T, Ito M: Am J Reprod Immunol 2010; 63: 601-610.
Document 4: Kwak-Kim J, Chung-Bang H S, Ng S C, Ntrivalas E I, Mangubat C P, Beaman K D, Beer A E, Gilman-Sachs A: Hum Reprod 2003; 18: 767-773.
Document 5: Ng S C, Gilman-Sachs A, Thakar P, Beaman K D, Beer A E, Kwak-Kim J: Am J Reprod Immunol 2002; 48: 77-86.
Document 6: Riley J K: Immunol Invest 2008; 37: 395-426.
Document 7: Goring S M, Lew A R, Ghement I, Kasekar A, Eyaow O, L'italien G J, Kasiske B: Curr Ned Res Opin 2014; 30: 1473-1487.
Document 8: Uchida K: Transplantation Now 2006; 19: 380-389.
Document 9: Kino T, Hatanaka H, Miyata S, Inamura N, Nishiyama M, Yajima T, Goto T, Okuhara M, Kohsaka M, Aoki H, Ohiai T: J Antibiot 1987; 40: 1256-1265.
Document 10: Ram R, Gafter-Gvili A, Yeshuru M, Paul M, Raanani P, Shpilberg O: Bone marrow transplant 2009; 43: 643-653.
Document 11: Ramiro S, Gaujoux-Viala C, Nam J L, Smolen J S, Buch M, Gossec L, van der Heijde D, Winthrop K, Landewe R: Ann Rheum Dis 2014; 73: 529-535.
Document 12: Nakagawa K, Nishi Y, Sugiyama R, Jyuen H, Takahashi C, Ojiro Y, Kuribayashi Y, Sugiyama R: Reprod Med Biol 2012; 11: 85-9.
Document 13: Sugiyama R, Nakagawa K, Shirai A, Sugiyama R, Nishi Y, Kuribayashi Y, Inoue M: J Assist Reprod Genet; 2010; 27: 161-7.
Document 14: Nakagawa K, Takahashi C, Nishi Y, Jyuen H, Sugiyama R, Kuribayashi Y, Sugiyama R: J Assist Reprod Genet 2012; 431 29: 679-85.
Document 15: Simon A, Laufer N: J Assist Reprod Genet 2012; 9:1227-1239.
Document 16: Garrido-Gomez T, Ruiz-Alonso M, Blesa D, Diaz-Gimeno P, Vilella F, Simon C: Fertil Steril 2013; 99: 1078-85.
Document 17: Clark D A, Coulam C B, Striker R B: J Assist Reprod Genet 2006; 23:1-13.
Document 18: Virro M R, Winger E E, Reed J L: Am J Reprod Immunol 2012; 68: 218-225.
Document 19: Graphou O, Chioti A, Pantazi A, Tsukoura C, Kontopoulou V, Guorgiadou E, Balafoutas C, Koussoulakos S, Margaritis L H, Varla-Leftherioti M: Am J Reprod Immunol 2003; 49: 21-29.
Document 20: Mangubat C P, Thaler P P, Cavalcante M, Kwak-Kim J Y H, Beer A E: Am J Reprod Immunol 2001: 45: 24.
Document 21: Winger E E, Reed J L, Ashoush S, El-Toukhy T, Ahuja S, Taranissi M: Am J Repro Immunol 2011; 65: 610-618.
Document 22: Carter J D, Ladhani A, Ricca L R, Valeriano J, Vasey F B: J Rheumatol 2009; 36: 635-641.
Document 23: Tan B K, Vandekerckhove P, Kennedy R, Keay S D: BJOG 2005; 112: 460 773-780.

Document 24: Kalu E, Bhaskaran S, Thum M Y, ishwanatha R, Croucher C, Sherriff E, Ford B, Bansal A S: Am J Reprod Immunol 2008; 59: 206-211.

Document 25: Liu H Y, Liu Z K, Chao H, Li Z, Song Z, Yang Y, Peng J P: J Interferon Cytokine Res 2014; 34: 394-403.

Document 26: Liu Z K, Wang R C, Han B C, Yang Y, Peng J P: PLoS One 2012; 7: e45224.

Document 27: Ashkar A, Di Santo J P, Croy B A. J Exp Med 2000; 192: 259-270.

Document 28: Ostensen M, Forger F: Curr Opin Pharmacol 2013; 13: 470-475.

Document 29: Liu J, Farmer J D Jr, Lane W S, Friedman J, Weissman I, Schreiber S L: Cell 1991; 66: 807-815.

Document 30: Rath T: Expert Opin Pharmacother 2013; 14:115-122.

Document 31: Abou-Jaoude M M, Najm R, Shaheen J, Nawfal N, Abboud S, Alhabash M, Darwish M, Mulhem A, Ojjeh A, Almawi W Y: Transplantation Proceedings 2005; 37: 484 3025-3028.

Document 32: Ogiwara D: Transplantation Now 2004; 17: 451-455.

Document 33: Coscia L A, Constantinescu S, Moritz M J, Frank A M, Ramirez C B, Maley W R, Doria C, McGrory C H, Allenti V T: Clinical Transplants 2010: 65-85.

Document 34: Wong K M, Mastenbroek S, Repping S: Fertil Steril 2014; 102: 493 19-26.

Document 35: Sibai B M, Ramadan M K, Usta I, Salama M, Mercer B M, Friedman S A. Maternal morbidity and mortality in 442 pregnancies with hemolysis, elevated liver enzymes, and low platelets (HELLP syndrome) Am J Obstet Gynecol. 1993; 169:1000-6.

Document 36: Sibai B, Dekker G, Kupferminc M. Preeclampsia. Lancet. 2005; 365:785-99.

Document 37: Saito S, Sakai M. Th1/Th2 balance in preeclampsia. J Reprod Immunol. 2003; 59:161-73.

Document 38: Y Sasaki, D Darmochwal-Kolarz, D Suzuki, M Sakai, M Ito, T Shima, and others. Proportion of peripheral blood and decidual CD4+ CD25bright regulatory T cells in pre-eclampsia. Clin Exp Immunol. 2007; 149: 139-145.

Document 39: Szarka A, Rigó J, Lázár L, Bekö G, and Molvarec A. Circulating cytokines, chemokines and adhesion molecules in normal pregnancy and preeclampsia determined by multiplex suspension array. BMC Immunol. 2010; 11: 59.

Document 40: Powe C E, Levine R J, Karumanchi S A. Preeclampsia, a disease of the maternal endothelium: the role of antiangiogenic factors and implications for later cardiovascular disease. Circulation. 2011; 123:2856-69.

Document 41: Darmochwal-Kolarz D, Kludka-Sternik M, Tabarkiewicz J, Kolarz B, Rolinski J, Leszczynska-Gorzelak B, and others. The predominance of Th17 lymphocytes and decreased number and function of Treg cells in preeclampsia. J Reprod Immunol. 2012; 93:75-81.

Document 42: Chaiworapongsa T, Chaemsaithong P, Yeo L, Romero R. Pre-eclampsia part 1: current understanding of its pathophysiology. Nat Rev Nephrol. 2014; 10:466-80.

Document 43: Mol B W J, Roberts C T, Thangaratinam S, Magee L A, de Groot C J M, Hofmeyr G J. Pre-eclampsia. Lancet. 2016; 387:999-1011.

Document 44: Salazar Garcia M D, Mobley Y, Henson J, Davies M, Skariah A, Dambaeva S, and others. Early pregnancy immune biomarkers in peripheral blood may predict preeclampsia. J Reprod Immunol. 2018; 125:25-31.

Document 45: Yamaguchi K. Tacrolimus treatment for infertility related to maternal-fetal immune interactions. Am J Reprod Immunol. 2019; 81:e13097.

Document 46: Nakagawa K, Kwak-Kim J, Ota K, Kuroda K, Hisano M, Sugiyama R, Yamaguchi K. Immunosuppression with Tacrolimus Improved Reproductive Outcome of Women with Repeated Implantation Failure and Elevated Peripheral Blood Th1/Th2 Cell Ratios. Am J Reprod Immunol. 2015; 73: 353-61.

Document 47: Rolnik D L, Wright D, Poon L C, O'Gorman N, Syngelaki A, de Paco Matallana C, and others. Aspirin versus Placebo in Pregnancies at High Risk for Preterm Preeclampsia. N Engl J Med. 2017; 377:613-622.

Example 2

Materials and Methods
Subject Group for Research

Among women who were capable of IVF/ET and had a history of three or more consecutive miscarriages, stillbirths, or intrauterine fetal growth retardations, eleven infertilitas patients who could not bear child even though they received one or more times of existing treatment, were selected as subjects. These patients were a group of patients for whom clear findings of abnormality related to infertility were not recognized with a serological examination that had been performed in advance.

The patients were evaluated through a transvaginal ultrasound examination, a Fallopian tube patency test, and hysteroscopy before an index ART cycle. Among the participants, no one had submucosal myoma, endometrial polyps, intrauterine adhesion, congenital abnormalities in the uterus, or hydrosalpinx. Also, any pregnant women, or any women exhibiting chronic medical symptoms or inflammatory symptoms were excluded from the subjects. Any women who had experienced miscarriage in the previous IVF cycle, who had received an IVF cycle, or who had received vaccination, all within three months, were excluded from the subjects. Any women with acquired or congenital thrombophilia were excluded from the subjects.

Analysis of Th1 Cells and Th2 Cells

The analysis was carried out according to the method described in Example 1. However, the determination of the Th1/Th2 cell ratio in a patient was carried out immediately after establishment of pregnancy (the day of confirming establishment of pregnancy). The level of the Th1/Th2 cell ratio was determined according to the average value +1 standard deviation method in the same manner as in Example 1, and a Th1/Th2 cell ratio that was equal to 10.3 or higher than that was classified as an increased Th1/Th2 cell ratio.

Treatment with Tacrolimus

All of the eleven patients were subjected to treatment with tacrolimus in the same manner as in Example 1, except for the duration of administration. The dose of tacrolimus was 1 mg per day for patients who had a Th1/Th2 cell ratio of 10.3 or higher and lower than 13.0 (four patients); the dose was 2 mg per day for patients who had a Th1/Th2 cell ratio of 13.0 or higher and lower than 15.8 (three patients); and the dose was 3 mg per day for patients who had a Th1/Th2 cell ratio of 15.8 or higher (four patients). The duration of administration of tacrolimus was from the time point immediately after establishment of pregnancy was confirmed by a pregnancy test and the Th1/Th2 cell ratio was checked, until the day of delivery, in all cases.

IVF-ET Treatment

The treatment was carried out in the same manner as in Example 1.

Statistical Analysis

The analysis was carried out in the same manner as in Example 1.

Results

The features of the patients who received the treatment are summarized in Table 5.

The results of the treatment are summarized in Table 6. Eight out of the eleven patients who received the treatment obtained healthy babies by full term birth. Premature birth case 1 disclosed herein is a case with a history of 10 or more times of miscarriage due to resistance to all the therapeutic methods that are currently implemented, as described in the Background Art. Other therapeutic methods were not used in combination, and childbearing was achieved by the treatment with tacrolimus alone.

TABLE 5

|  | Treatment group (n = 11) |
|---|---|
| Age (years) | 37.3 ± 3.6 |
| Medical history of pregnancy % (n) | |
| No | 0 (0) |
| Yes | 100 (11) |
| History of pregnancy | |
| Number of times of pregnancy | 4.8 ± 2.5 |
| Number of times of childbearing (live born baby) | 0.2 ± 0.4 |

TABLE 6

|  | Miscarriage | Premature birth | Full term birth |
|---|---|---|---|
| Number of newborn babies (n) | 2 | 1 | 8 |
| Mode of delivery | | | |
| Vaginal delivery (n) | — | 0 | 8 |
| Cesarean section (n) | — | 1 | 0 |
| Number of gestational days (days) | — | 208 | 279.3 ± 6.0 |
| Birth weight (gm) | — | 748 | 3149 ± 234 |
| Gender of baby male/female (n/n) | — | 0/1 | 4/4 |
| APGAR Score 1 minute | — | 6 | 8.0 ± 1.0 |
| APGAR Score 5 minute | — | 8 | 9.0 ± 0.5 |
| Umbilical cord blood pH | — | 7.304 | 7.3 ± 0.12 |
| Length of umbilical cord (cm) | — | 27.5 | 62.4 ± 12.9 |
| Complications of mother | — | 1 (Pregnancy-induced hypertension) | 0 |
| Complications of newborn baby | — | 1 (Low birth weight baby) | 0 |

Example 3

Materials and Methods

Subject Group for Research

Women who were capable of IVF/ET, and had a history of having pregnancy-induced hypertension syndrome during the previous gestation, or showed a clinical finding of being susceptible to the development of pregnancy-induced hypertension syndrome, were selected as subjects. Once pregnancy-induced hypertension syndrome develops, the possibility of experiencing repeated onset in the subsequent gestations is very high.

The patients were evaluated through a transvaginal ultrasound examination, a Fallopian tube patency test, and hysteroscopy before an index ART cycle. Any pregnant women, or any women exhibiting chronic medical symptoms or inflammatory symptoms were excluded from the subjects. Any women who had experienced miscarriage in the previous IVF cycle, who had received an IVF cycle, or who had received vaccination, all within three months, were excluded from the subjects. Any women with acquired or congenital thrombophilia were excluded from the subjects.

Treatment with Tacrolimus

All the patients were subjected to treatment with tacrolimus in the same manner as in Example 2. The dose of tacrolimus was 1 mg to 3 mg per day. The duration of administration of tacrolimus was from the time point immediately after establishment of pregnancy was confirmed by a pregnancy test, until the day of delivery, in all cases. In Case 1 and Case 3 described below, 3 mg of tacrolimus per day was administered everyday from the time point immediately after establishment of pregnancy was confirmed and until the second trimester of pregnancy, and 2 mg of tacrolimus per day was administered everyday from the third trimester of pregnancy until the delivery. In Case 2 described below, 2 mg of tacrolimus per day was administered everyday from the time point immediately after establishment of pregnancy was confirmed and until the delivery.

IVF-ET Treatment

The treatment was carried out in the same manner as in Example 2.

Statistical Analysis

The analysis was carried out in the same manner as in Example 2.

Confirmation of Results

The effects of administering tacrolimus were evaluated on the basis of whether the patients satisfactorily maintained the state of pregnancy without developing pregnancy-induced hypertension syndrome at predetermined time points between the second trimester and the third trimester of pregnancy. Cases in which the evaluation has been roughly completed are as follows.

In a case in which intrauterine fetal death occurred in week 38 of pregnancy due to pregnancy-induced hypertension syndrome in the previous gestation (Case 1), the patient did not experience an increase in blood pressure as a result of administration of tacrolimus and gave birth to a healthy baby in week 39. In a case of twin pregnancy with infertilitas and positive anti-phosphorus antibody, with a high potential of developing pregnancy-induced hypertension syndrome (Case 2), the patient did not experience an increase in blood pressure as a result of administration of tacrolimus and gave birth to a healthy baby in week 35 (premature rupture of the membrane caused by cough, premature birth of twin). Furthermore, in a case in which the patient had edema from week 25, experienced an increase in blood pressure from week 28, was diagnosed as pregnancy-induced hypertension syndrome, and suffered intrauterine fetal death in week 32 in the previous gestation (Case 3), the patient is currently passing week 34 of pregnancy auspiciously without edema and without a tendency of blood pressure increase, as a result of administration of tacrolimus.

During the progress of pregnancy, babies grew satisfactorily in all cases, and abnormalities were not observed in both the mother and the child.

Example 4

Materials and Methods
Subject Group for Research

The patient was a 38 year old (y.o.) female with a past history of both eclampsia and HELLP syndrome. During the first pregnancy when the patient was 32 y.o., she complained of physical deconditioning from early in her pregnancy. Pretibial edema, weight-gain, and a tendency toward high blood pressure were observed at 15 weeks gestation. Sudden aggravation of the edema, proteinuria and hypertension appeared at 18 weeks gestation, at which time she was diagnosed with preeclampsia. HELLP syndrome and eclampsia occurred at 20 weeks gestation and a stillbirth required an emergency cesarean section. After delivery of the baby, she had severe complications such as pulmonary edema, disseminated intravascular coagulation, and intraperitoneal bleeding. She was medicated via an artificial respirator, and received albumin and a blood transfusion (Table 6).

struction and caused fetal growth retardation and hypertension. The patient was treated with 1 mg/day of tacrolimus to control the maternal-fetal immunity.

The course of the pregnancy was stable with no emergence of proteinuria, edema or hypertension until 32 weeks gestation. Nevertheless, proteinuria and a rise in blood pressure emerged the next week, and HELLP syndrome occurred 3 days after these symptoms (Table 6). A caesarean section was performed at 33 weeks and 3 days gestation, at which time the patient delivered a male baby weighing 1,490 g.

During pregnancy, the immunological findings showed a decrease in the Th1 and Th2 cell populations in CD4 positive cells with time, while the NK cell activity (normal range, 18-40%) was decreased in the $2^{nd}$ trimester and then obviously increased at 32 weeks gestation (FIG. 1).

Treatment with Tacrolimus

This patient received a monotherapy of tacrolimus without a concomitant treatment of a low dose of aspirin, which is often used as an anti-platelet agent for HDP[47]. The course

TABLE 6

Comparing the outcomes without and with tacrolimus treatment

|   |   | Previous pregnancy (without tacrolimus treatment) | | Current pregnancy (with tacrolimus treatment) | |
|---|---|---|---|---|---|
|   |   | before deliverly | after deliverly | before deliverly | after deliverly |
| Symptoms | edema | significant | significant | slight | slight |
|   | start of proteinuria (weeks gstation) | 18 |   | 33 |   |
|   | hypertension | significant | significant | not observed | transient |
|   | complications after deliverly |   | pulmonary edema DIC intraabdominal hemorrhage with infection |   | none |
| Treatments |   | Ca antagonists magnesium sulfate | Ca antagonists magnesium sulfate respiratory care using respirator albmin transfusion blood transfusion (RBC, FFP, PLT) | none | magnesium sulfate (perioperative periods) |
| Blood examitaion | AST (U/L) | 1141 | 959 | 65 | 898 |
|   | ALT (U/L) | 891 | 729 | 71 | 833 |
|   | LDH (U/L) | 1968 | 1857 | 316 | 1995 |
|   | Cr (mg/dL) | 1 | 0.96 | 1 | 0.59 |
|   | WBC (µl) | 12200 | 11700 | 8280 | 8220 |
|   | Hb (g/dL) | 14.9 | 12.6 | 11 | 10.5 |
|   | Plt ($10^4$/µL) | 4.2 | 2.8 | 10 | 2.2 |
| Fetal information | Gestational age |   | 20 W 0 d |   | 33 W 3 d |
|   | body wieght (g) |   | 138 |   | 1490 |
|   | fetal growth |   | −2.0 SD |   | −1.9 SD |

Her blood tests before her present pregnancy showed no abnormalities in liver function, renal function or in blood coagulation ability. Laboratory findings related to infertility such as antiphospholipid syndrome (anti-CL IgG Ab, anti-CL IgM Ab, anti-β2GP-1 Ab, anti-PS/PT Ab, anti-PE IgG Ab, anti-PE IgM Ab), autoimmune disease (ANA and anti-DNA Ab), and disorders of blood coagulation (protein S activity, protein C activity, factor XII activity) were all negative.

Although no obvious immunological abnormalities of the Th1(CD4+IFN-γ+)/Th2 (CD4+IL-4+) cell ratio (15.2/2.1) in CD4 positive cells (normal range, <10.3) were observed before pregnancy[46], it was assumed that maternal immunity would be activated by the embedding of a fertilized ovum (recognition of fetal antigens) and the abnormalities of maternal-fetal immunity may have inhibited placenta conof the pregnancy was stable until the 3rd trimester, and no significant symptoms were observed during the $2^{nd}$ trimester, at which point HELLP syndrome occurred in her previous pregnancy. Clinical signs of HELLP syndrome rapidly appeared, however, at 33 weeks gestation. A decrease in the Th1 and Th2 cell populations in CD4 positive cells and a reduction in the activity of NK cells over time post-partum were observed, which confirms that the tacrolimus regimen exerted sufficient suppressive effect on those cells, whereas the activity of NK cells was elevated at 32 weeks gestation. A possibility was speculated that NK cell activity was stimulated when a large number of fetal antigens were transferred to the maternal blood circulation after the suppression of the NK cells by the 1 mg/day dose of tacrolimus became insufficient in the $3^{rd}$ trimester. An assessment of the activation of T cells without Treg cells showed the same timing even though the population was not altered.

The imaged mechanisms of clinical expression were tantamount to a repeated episode of HELLP syndrome in the same patient. HELLP syndrome and Eclampsia are known as severe complications in HDP. This patient had both diseases in an earlier pregnancy without treatment, which resulted in a stillbirth. Although the reoccurrence of HELLP syndrome was conclusive, tacrolimus treatment helped the patient evade clinical expression early in her pregnancy, which prolonged the timing of onset until about 13 weeks gestation.

Recognition of fetal antigens is enhanced after the first pregnancy in infertility patients with an immunological abnormality. Therefore, earlier onsets of HELLP syndrome and eclampsia with aggravation of HDP were expected in a subsequent pregnancy. Conversely, tacrolimus treatment clearly prolonged the disease expression, since other concomitant treatments were not performed during this pregnancy. It was apparent that better construction and function of the placenta was achieved via suppressing the activation of maternal immune rejection against the fetus, which thereby induced maternal tolerance for the fetus and prevented both hypertension and fetal growth retardation during the pregnancy. In order to achieve a full-term delivery and promote fetal growth, the dose of tacrolimus could be adjusted by, for example, increasing or decreasing.

Th1 and Th2 cell populations in CD4 positive cells and the NK cell activity were measured to evaluate the patient's pathological condition. One of the parameters, NK cell activity, indicated an appearance of abnormal maternal-fetal immunity. Other parameters that can be used to evaluate the failure of maternal tolerance for a fetus and activation of maternal immune rejection against a fetus with inflammation include Treg cells, Th17 cells, cytokines, and chemokines[37-44].

The embodiments of present invention are not intended to be limited to the various embodiments and the various Examples described above, various modifications can be made to the extent that is disclosed in the claims, and embodiments obtainable by appropriately combining the technical means respectively disclosed in different embodiments and different Examples are also included in the technical scope of the present invention. Furthermore, new technical features can be formed by combining the technical means respectively disclosed in the various embodiments and the various Examples.

What is claimed is:

1. A method for ameliorating a pregnancy-induced hypertension syndrome in a subject in need thereof, comprising administering a medicament comprising tacrolimus or a pharmaceutically acceptable salt thereof as an active ingredient in a therapeutically effective amount to the subject.

2. The method according to claim 1, wherein the therapeutically effective amount of the active ingredient is 5 mg or less per day.

3. The method according to claim 1, wherein the therapeutically effective amount of the active ingredient is in the range of from 1 mg to 3 mg per day.

4. The method according to claim 1, wherein the subject has an increased Th1/Th2 cell ratio compared to a pregnant subject who does not have the pregnancy-induced hypertension syndrome.

5. The method according to claim 1, wherein the subject is subjected to transplantation of an embryo obtained by in vitro fertilization.

6. The method according to claim 1, wherein the medicament is administered at least during a period from 1 day before or 2 days before the implantation of a fertilized ovum or a transplanted embryo into the endometrium to 0 days after the implantation.

7. The method according to claim 1, wherein the pregnancy-induced hypertension syndrome is a defective pregnancy condition, and the medicament is administered at least for a period from the establishment to the $200^{th}$ day of pregnancy.

8. The method according to claim 1, wherein the ameliorating is preventing the pregnancy-induced hypertension syndrome.

9. The method according to claim 1, wherein the subject is subjected to an artificial insemination treatment or an administration of a fertility medicine.

* * * * *